US006410714B1

(12) United States Patent
Weber et al.

(10) Patent No.: US 6,410,714 B1
(45) Date of Patent: Jun. 25, 2002

(54) CANINE LOW AFFINITY IGE RECEPTOR (CD23) NUCLEIC ACID MOLECULES AND USES THEREOF

(75) Inventors: Eric R. Weber, Fort Collins; Catherine A. McCall, Boulder, both of CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/535,521

(22) Filed: Mar. 24, 2000

Related U.S. Application Data

(60) Provisional application No. 60/125,913, filed on Mar. 24, 1999.

(51) Int. Cl.[7] .................. C07H 21/04; C12N 15/09; C12N 15/63
(52) U.S. Cl. ............... 536/23.5; 536/23.1; 435/69.1; 435/455; 435/471; 435/235.1; 435/252.3; 435/320.1
(58) Field of Search ............... 536/23.1, 23.5; 435/69.1, 69.6, 455, 471, 252.3, 320.1, 235.1

(56) References Cited

U.S. PATENT DOCUMENTS

| 5,081,028 A | * | 1/1992 | Hofstetter et al. |
| 5,236,706 A | * | 8/1993 | Debre et al. |
| 5,766,943 A | * | 6/1998 | Lynch et al. |

FOREIGN PATENT DOCUMENTS

| WO | WO 00/15260 | 3/2000 |

OTHER PUBLICATIONS

GenBank Accession No. X04772. Human mRNA for low affinity IgE receptor. Sep. 12, 1993.*
Bartlett et al., *J. Immunol.*, 1995, vol. 154, No. 9, pp. 4240–4246.
Bonnefoy et al., *Immunology Today*, 1996, vol. 17, No. 9, pp. 418–420.
Bonnefoy et al., *Eur Respir J*, 1996, vol. 9, Suppl. 22, pp. 63s–66s.
Christie et al., *Eur. J. Immunol*, 1997, vol. 27, pp. 3228–3235.
Clynes et al., *Proc. Natl. Acad. Sci. USA*, 1998, vol. 95, pp. 652–656.
Conrad et al., *Biochem Soc Trans*, 1997, vol. 25, No. 2, pp. 393–397.
Dunphy et al., *Mod Pathol*, 1997, vol. 10, No. 8, pp. 818–822.
Flores–Romo et al., *Science*, 1993, vol. 261, pp. 1038–1041.
Fujiwara et al., *Proc. Natl. Acad. Sci. USA*, 1994, vol. 91, pp. 6835–6839.
Hewitt et al., *J. Exp. Med.*, 1995, vol. 182, pp. 1537–1544.
Kelly et al., *The Journal of Immunology*, 1998, vol. 161, No. 12, pp. 6696–6704.
Kljaic–Turkalj et al., *Int Arch Allergy Immunol.*, 1996, vol. 111, pp. 188–194.
Knauf et al., *Leukemia and Lymphoma*, 1997, vol. 27, pp. 523–532.
Lamers et al., *Immunol Rev*, 1995, vol. 148, pp. 71–95.
Latchman et al., *British Journal of Dermatology*, 1995, vol. 132, pp. 592–598.
Luo et al., *The Journal of Immunology*, 1991, vol. 146, No. 7, pp. 2122–2129.

* cited by examiner

*Primary Examiner*—Phillip Gambel
*Assistant Examiner*—Jessica H. Roark
(74) *Attorney, Agent, or Firm*—Heska Corporation

(57) ABSTRACT

The present invention relates to canine low affinity IgE receptor (CD23) nucleic acid molecules, proteins encoded by such nucleic acid molecules, antibodies raised against such proteins, compounds capable of regulating, e.g., inhibiting or activating, the function of such proteins, and methods to identify such regulatory compounds. The present invention also includes therapeutic compositions comprising such nucleic acid molecules, proteins, antibodies, or regulatory compounds, methods to use such therapeutic compositions, and methods and kits to detect CD23 proteins.

11 Claims, No Drawings

CANINE LOW AFFINITY IGE RECEPTOR (CD23) NUCLEIC ACID MOLECULES AND USES THEREOF

CROSS REFERENCE TO RELATED APPLICATIONS

This application claims priority to U.S. Provisional Patent Application Serial No. 60/125,913, entitled "Novel Canine Low Affinity IgE Receptor (CD23) Proteins, Nucleic Acid Molecules and Uses Thereof", filed Mar. 24, 1999.

FIELD OF THE INVENTION

The present invention relates to canine low affinity IgE receptor (CD23) nucleic acid molecules, proteins encoded by such nucleic acid molecules, antibodies raised against such proteins, compounds capable of regulating, e.g. inhibiting or activating, the function of such proteins, and methods to identify such regulatory compounds. The present invention also includes therapeutic compositions comprising such nucleic acid molecules, proteins, antibodies, or regulatory compounds, as well as methods and kits to detect such proteins.

BACKGROUND OF THE INVENTION

Immunoglobulin E (IgE) is an important molecule in the establishment and progression of allergic disease in an animal. IgE antibody mediates allergy related diseases, for example atopic dermatitis, asthma, inflammation, hay fever, and food sensitivities. The presence of IgE or elevated levels of IgE in an animal is indicative of such diseases.

Recently, it has been shown in humans and in mice that CD23, or low-affinity IgE receptor, has a role in the regulation of IgE levels. For example, CD23 present on B cells, when bound by IgE, transduces a feedback-inhibitory signal that prevents further IgE synthesis. Additionally, CD23 present on antigen presenting cells can interact with antigen IgE complexes, causing internalization of the antigen-IgE complex, more efficient presentation of the antigen to T cells, and an enhanced response to the antigen. This phenomenon is called IgE-mediated antigen presentation, and can be responsible for antigen sensitization and development of allergies. A soluble form of CD23, referred to as sCD23, may regulate immune and/or inflammatory responses. This soluble form of CD23 is capable of binding to IgE-producing B cells, apparently via IgE or a receptor called CD21, and causing up-regulation of IgE production in that B cell. In yet another role, soluble CD23 can interact with inflammatory cells, such as monocytes and macrophages, apparently via the receptors CD11b and CD11c on the surface of the inflammatory cells, causing the inflammatory cells to elaborate proinflammatory cytokines, for example interleukin-1 alpha, interleukin-6, and interferon gamma.

Until the discovery of the present invention, intervention in allergic diseases in canids, or dogs, by manipulating the regulation of IgE levels in dogs or IgE-mediated antigen presentation by CD23 has been hindered by the absence of reagents capable of such action. Additionally, detection of CD23 levels in canids has been hindered by the absence of suitable reagents for detection of CD23.

Prior investigators have disclosed nucleic acid sequences encoding: the human low affinity IgE receptor, also known as human CD23, (Ikuda, et al., *Proc. Natl. Acad. Sci.* vol. 84, p 819–823, 1987; Kikutani, *Cell,* vol. 47, pp 657–660, 1986; Ludin, C. et al., *Embo J*. vol. 6, pp 109–113, 1987; and others); the mouse low affinity IgE receptor, also known as mouse CD23, Nunez, et al. *Pathobiology* vol. 61, pp 128–137, 1993; and the rat low affinity IgE receptor, also known as rat CD23, (Genbank accession number X73579, 1993.) Although the human CD23 was known as early as 1986, it has never been used to identify a canine CD23 nucleic acid sequence or protein. Similarly, although nucleic acid sequences encoding rat and mouse CD23 have been known since 1993, they have never been used to identify a nucleic acid sequence, encoding the canine CD23 protein or nucleic acid molecule. Moreover, the determination of the nucleic acid sequences of human, rat and mouse CD23 genes and/or cDNAs does not indicate, suggest or predict the cloning of a novel CD23 gene from a different species, in particular, from a canine species.

Thus, products and processes of the present invention are needed in the art that will provide specific detection of CD23 and treatment of CD23-mediated disease in canids, including, but not limited to, domestic dogs.

SUMMARY OF THE INVENTION

The present invention relates to a novel product and process for protection of canids from diseases mediated by canine low affinity IgE receptor, also known as canine CD23. Identification of a CD23 of the present invention is unexpected because initial attempts using the primers containing the most similar nucleic acid sequences identified by previous investigators failed.

According to the present invention there are provided canine CD23 proteins, and derivatives thereof; canine CD23 nucleic acid molecules, including those that encode such proteins; antibodies raised against such CD23 proteins (i.e. anti-CD23 antibodies); and compounds that regulate, i.e. inhibit or activate, CD23 production or activity.

The present invention also includes methods to obtain such proteins, derivatives, nucleic acid molecules, antibodies and regulatory compounds. Also included in the present invention are therapeutic compositions comprising a protective compound derived from a protein of the present invention that inhibits or activates the activity of canine CD23 as well as methods to use such therapeutic compositions to reduce allergy or inflammation. Also included in the present invention are novel methods to detect canine CD23, and an assay kit for detecting the presence of canine CD23.

One embodiment of the present invention is an isolated nucleic acid molecule having a length greater than or equal to about 150 nucleotides which hybridizes under conditions that allow less than or equal to about a 10% base pair mismatch with a nucleic acid sequence selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26; or a fragment thereof having at least about 47 nucleotides.

Another embodiment of the present invention is an isolated nucleic acid molecule selected from the group consisting of a nucleic acid comprising a nucleic acid sequence selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26; and a nucleic acid molecule comprising an at least 30 nucleotide portion identical in sequence to a consecutive 30 nucleotide portion of at least one of the sequences named above.

The present invention also relates to recombinant molecules, recombinant viruses and recombinant cells that include a canine CD23 nucleic acid molecule of the present invention. Also included are methods to produce such nucleic acid molecules, recombinant molecules, recombinant viruses and recombinant cells.

Another embodiment of the present invention includes an isolated canine CD23 protein selected from the group consisting of (a) a protein comprising an amino acid sequence that is at least about 70% identical to an amino acid sequence selected from the group consisting of SEQ ID NO:2, SEQ ID NO:5, SEQ ID NO:8, SEQ ID NO:1, SEQ ID NO:14, SEQ ID NO:17, SEQ ID NO:20 and/or SEQ ID NO:25, wherein said protein is at least about 80 amino acids in length; (b) a protein comprising an amino acid sequence having SEQ ID NO:2, SEQ ID NO:5, SEQ ID NO:8, SEQ ID NO:11, SEQ ID NO:14, SEQ ID NO:17, SEQ ID NO:20 and/or SEQ ID NO:25, or a protein comprising a fragment thereof, wherein said fragment is capable of binding to IgE;(c) a protein comprising an amino acid sequence having SEQ ID NO:2, SEQ ID NO:5, SEQ ID NO:8, SEQ ID NO:11 SEQ ID NO:14, SEQ ID NO:17, SEQ ID NO:20 and/or SEQ ID NO:25, or a protein comprising a fragment thereof, wherein said fragment is capable of binding to a receptor selected from the group consisting of CD21, CD11b and CD11c; and (d) a protein encoded by an allelic variant of a nucleic acid molecule encoding any protein of (a), (b), and/or (c).

The present invention also relates to derivatives of canine CD23 proteins as well as to isolated antibodies that selectively bind to canine CD23 proteins or derivatives thereof. Also included are methods, including recombinant methods, to produce proteins, derivatives, and antibodies of the present invention.

Included in the present invention is a therapeutic composition that reduces allergy or inflammation in a canid. One embodiment includes a therapeutic composition that is capable of reducing the amount and/or activity of IgE present in a canid. Such a therapeutic composition includes one or more of the following therapeutic compounds: an isolated canine CD23 protein; a substrate analog of an isolated canine CD23 protein; a mimetope of an isolated CD23 protein; an isolated antibody that selectively binds to a canine CD23 protein; and other regulatory compounds, e.g. an inhibitor or activator, that regulate CD23 activity, usually by binding to, or otherwise interacting with or otherwise modifying CD23 activity. CD23 activity includes binding of soluble CD23 to a B cell, binding of soluble CD23 to an inflammatory cell, binding of IgE to CD23 on an antigen presenting cell, binding of soluble CD23 to IgE, and/or binding of IgE to CD23 on a B cell. A method of the present invention includes the step of administering to a canid a therapeutic composition of the present invention.

The therapeutic composition can perform a number of functions, all related to regulating CD23 amounts and/or activity in a canid. The functions of the therapeutic composition can include one or more of the following: (a) activating CD23 present on B cells; (b) reducing the binding of soluble CD23 to a receptor on B cells; (c) reducing the binding of soluble CD23 to an inflammatory cell; and (d) reducing the binding of an IgE-antigen complex to CD23 on an antigen presenting cell.

Included in the present invention is a method to identify a compound capable of regulating the activity of CD23 in an canid. Such a method comprises: (a) contacting an isolated canine CD23 protein with a putative regulating compound, under conditions in which, in absence of said compound, said protein has CD23 activity, and (b) determining if the compound regulates such activity.

The present invention also includes a method to detect the presence of CD23 in a canid. Such a method includes the steps of: (a) contacting a putative CD23 containing biological sample with an antibody to canine CD23 or another molecule capable of selective binding to CD23, under conditions suitable for the formation of an antibody-CD23 complex or other type of protein-CD23 complex, and (b) determining the presence of said CD23 by detecting said complex, the presence of said complex indicating the presence of said CD23. CD23 to detect includes soluble CD23.

The present invention also includes a kit to test if a canid has or is susceptible to allergy or inflammation by testing for the presence of CD23 in the canid. Elevated levels of CD23 indicates the presence of allergy or inflammation in a canid. The kit comprises a molecule that is capable of selectively binding to a canine CD23 protein, i.e. a CD23 binding partner, and as such can include antibodies to CD23, CD23 receptors, and CD23 ligands. The kit also comprises a means for determining the presence of a complex of CD23 and the CD23 selectively binding molecule, wherein the means enables the detection of the complex. The detection of the complex indicates the presence of CD23 in a canid.

DETAILED DESCRIPTION

The present invention provides for isolated canine low affinity IgE receptor, also known as canine CD23, proteins, isolated canine CD23 nucleic acid molecules, antibodies directed against canine CD23 proteins, and compounds able to regulate the activity and/or amount of canine CD23 proteins, such as compounds able to reduce the activity and/or amount of canine CD23 proteins and compounds able to increase the activity and/or amount of canine CD23 proteins. As used herein, the terms isolated CD23 proteins and isolated CD23 nucleic acid molecules refer to canine CD23 proteins and CD23 nucleic acid molecules derived from canids, and, as such, can be obtained from their natural source or can be produced using, for example, recombinant nucleic acid technology or chemical synthesis. Canine CD23 nucleic acid molecules of known length are denoted "nCaCD23$_\#$", wherein "#" refers to the number of nucleotides in that molecule, and CD23 proteins of known length are denoted "PCaCD23$_\#$", wherein "#" refers to the number of amino acid residues in that molecule. The terms, "canine CD23", PCaCD23$_\#$" are inclusive of all forms of canine CD23 proteins of the present invention, including soluble forms. Soluble forms of canine CD23 proteins can also be denoted as "soluble CD23" or "sCD23". Soluble canine CD23 nucleic acid molecules, i.e. CD23 nucleic acid molecules that encode sCD23 proteins of known length, are denoted "nsCaCD23$_\#$", wherein "#" refers to the number of nucleotides in that molecule, and soluble canine CD23 proteins of known length are denoted "PsCaCD23$_\#$", wherein "#" refers to the number of amino acid residues in that molecule.

Also included in the present invention is the use of these proteins, nucleic acid molecules, antibodies, and regulatory compounds as therapeutic compositions to protect canids from diseases mediated by CD23. Also included in the present invention is the use of these proteins and antibodies in a method to detect CD23 in a canid. Other applications of the present invention are disclosed below.

Canine CD23 proteins and nucleic acid molecules of the present invention have utility because they represent novel reagents for developing compounds that regulate IgE and/or CD23 levels in a canid. Regulation of IgE and/or CD23 levels in a canid offers a treatment for allergic disease in the canid. The products and processes of the present invention are advantageous because they enable regulation, i.e. inhibition and/or activation, of processes in the canid that involve CD23 proteins, such as binding of IgE to membrane bound forms of CD23 on B cells and/or antigen presenting cells, and binding of soluble forms of CD23 to its receptors on B cells and/or inflammatory cells. Additionally, the products and processes of the present invention are advantageous because they enable the detection of canine CD23 and the regulation of canine CD23 activity associated with disease.

One embodiment of the present invention is an isolated protein comprising a canine CD23 protein. It is to be noted that the term "a" or "an" entity refers to one or more of that entity; for example, a protein, a nucleic acid molecule, an antibody or a therapeutic composition refers to "one or more" or "at least one" protein, nucleic acid molecule, antibody or therapeutic composition, respectively. As such, the terms "a", or "an", "one or more" and "at least one" can be used interchangeably herein. It is also noted that the terms "comprising", "including", and "having" can be used interchangeably.

As used herein, a canid refers to any member of the canid family, including domestic dogs, and wild canids such as wolves, foxes, and coyotes.

According to the present invention, an isolated, or biologically pure, protein is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated canine CD23 protein can be a full length protein or any homolog of such a protein. An isolated protein of the present invention, including a homolog, can be identified in a straight-forward manner by the protein's ability to bind to IgE and/or ability to bind to CD23 receptors on B cells or inflammatory cells. Examples of canine CD23 homolog proteins include canine CD23 proteins in which amino acids have been deleted, e.g. a truncated version of the protein, such as a peptide, inserted, inverted, substituted and/or derivatized, e.g. by glycosylation, phosphorylation, acetylation, myristoylation, prenylation, palmitoylation, amidation and/or addition of glycerophosphatidyl inositol such that the homolog is capable of binding IgE and/or CD23 receptors on B cells or inflammatory cells.

Canine CD23 homolog proteins can be the result of natural allelic variation or natural mutation. CD23 protein homologs of the present invention can also be produced using techniques known in the art including, but not limited to, direct modifications to the protein or modifications to the gene or cDNA encoding the protein using, for example, classic or recombinant DNA techniques to effect random or targeted mutagenesis.

Canine CD23 proteins of the present invention are encoded by canine CD23 nucleic acid molecules. As used herein, canine CD23 nucleic acid molecules include nucleic acid sequences related to natural canine CD23 genes. As used herein, a canine CD23 gene includes all regions such as regulatory regions that control production of a CD23 protein encoded by such a gene, such as, but not limited to, transcription, translation or post-translation control regions, as well as the coding region itself, and any introns or non-translated coding regions. As used herein, a gene that "includes" or "comprises" a sequence may include that sequence as one or more exons. As used herein, the term "coding region" refers to a continuous linear array of nucleotides that translates into a protein. A full-length coding region is that coding region that is translated into a full-length, i.e. a complete, protein as would be initially translated in its natural milieu, prior to any post-translational modifications.

One embodiment of the present invention is a canine CD23 nucleic acid molecule that includes one or more of the following nucleic acid sequences: the nucleic acid sequence SEQ ID NO:1 and/or SEQ ID NO:4, as well as the complements of these nucleic acid sequences, i.e. SEQ ID NO:3 and/or SEQ ID NO:6, respectively; and a soluble canine CD23 nucleic acid molecule that comprises the nucleic acid sequence SEQ ID NO:7, SEQ ID NO:10, SEQ ID NO:13, SEQ ID NO:16, SEQ ID NO:19 and/or SEQ ID NO:24, as well as the complements of any of these nucleic acid sequences, i.e. SEQ ID NO:9, SEQ ID NO:12, SEQ ID NO:15, SEQ ID NO:18, SEQ ID NO:21 and/or SEQ ID NO:26, respectively. These nucleic acid sequences are further described herein. For example, nucleic acid sequence SEQ ID NO:1 represents the deduced sequence of the coding strand of a canine cDNA, i.e. complementary DNA, denoted herein as canine CD23 nucleic acid molecule nCaCD23$_{2851}$, the cloning of which is disclosed in the examples. The complement of SEQ ID:1, represented herein by SEQ ID NO:3, refers to the nucleic acid sequence of the strand complementary to the strand having SEQ ID NO:1, which can be easily be determined by those skilled in the art. Likewise, a nucleic acid sequence complement of any nucleic acid sequence of the present invention refers to the nucleic acid sequence of the nucleic acid strand that is fully complementary to, i.e. can form a complete double helix with, the strand for which the sequence is cited. It should be noted that since nucleic acid sequencing technology is not entirely error-free, SEQ ID NO:1, as well as other nucleic acid and protein sequences presented herein, represents an apparent nucleic acid sequence of the nucleic acid molecule encoding a CD23 protein of the present invention.

The nucleic acid sequences of the coding strand and complementary strand of nCaCD23$_{2851}$ are represented herein as SEQ ID NO:1 and SEQ ID NO:3, respectively. Translation of SEQ ID NO:1 suggests that nucleic acid molecules nCaCD23$_{2851}$ encodes a full-length CD23 protein of about 292 amino acids, denoted herein as PCaCD23$_{292}$, the amino acid sequence of which is presented in SEQ ID NO:2, assuming an open reading frame having an initiation codon spanning from nucleotide 199 through nucleotide 201 of SEQ ID NO:1 and a stop codon spanning from nucleotide 1075 through nucleotide 1077 of SEQ ID NO:1. The coding region encoding PCaCD23$_{292}$, without the stop codon, is presented herein as nCaCD23$_{876}$, which has the nucleotide sequence SEQ ID NO:4 (the coding strand) and SEQ ID NO:6 (the complementary strand). Translation of SEQ ID NO:1 yields SEQ ID NO:5 (the same sequence as SEQ ID NO:2), assuming a first in-frame codon extending from nucleotide 1 to nucleotide 3 of SEQ ID NO:4.

Sequence analysis of SEQ ID NO:2 also revealed the following features: a putative mature chain, occurring as a membrane-bound form of canine CD23 extending from about residue 2 to about residue 292; a putative extracellular domain extending from about residue 48 to about residue 292; and a putative cytoplasmic domain extending from about residue 2 to about residue 21, and a putative transmembrane region extending from about residue 22 to about residue 47.

Sequence analysis of SEQ ID NO:2 revealed several putative soluble CD23 forms. These forms arise from putative proteolytic cleavages which are predicted based on certain cleavages that occur in the human CD23 protein, and homologies between the canine and human CD23 proteins. One embodiment is a sCaCD23 protein that extends from about residue 85 to about residue 292 of SEQ ID NO:2, designated SEQ ID NO:20, also designated PsCaCD23$_{208}$, encoded by nucleic acid molecule SEQ ID NO:19. The nucleic acid molecule encoding PsCaCD23$_{208}$ is designated as nsCaCD23$_{624}$, which has a coding strand designated SEQ ID NO:19 and a complement designated SEQ ID NO:21 Another embodiment of a sCaCD23 protein extends from about residue 106 to about residue 292 of SEQ ID NO:2, designated SEQ ID NO:17, also designated PsCaCD23$_{187}$, encoded by nucleic acid molecule SEQ ID NO:16. The nucleic acid molecule encoding PsCaCD23$_{187}$ is designated nCaCD23$_{561}$, which has a coding strand designated SEQ ID NO:16 and a complement designated SEQ ID NO:18. Another embodiment of a sCaCD23 protein extends from about residue 152 to about residue 292 of SEQ ID NO:2, designated SEQ ID NO:14, also designated PsCaCD23$_{141}$, encoded by nucleic acid molecule SEQ ID NO:13. The nucleic acid molecule encoding PsCaCD23$_{141}$ is designated nsCaCD23$_{423}$, which has a coding strand designated SEQ ID NO:13 and a complement designated SEQ ID NO:15. Another embodiment of a sCaCD23 protein extends from about residue 154 to about residue 292 of SEQ ID NO:2, designated SEQ ID NO:11, also designated PsCaCD23 $_{139}$, encoded by nucleic acid molecule SEQ ID NO:10 The nucleic acid molecule encoding PsCaCD23$_{139}$ is designated nCaCD23$_{417}$, which has a coding strand designated SEQ ID NO:10 and a complement designated SEQ ID NO:12. Yet another embodiment of a sCaCD23 protein extends from about residue 165 to about residue 292 of SEQ ID NO:2, designated SEQ ID NO:8, also designated PsCaCD23$_{128}$, encoded by nucleic acid molecule SEQ ID NO:7. The nucleic acid molecule encoding PsCaCD23$_{128}$ is designated nsCaCD23$_{384}$, which has a coding strand designated SEQ ID NO:7 and a complement designated SEQ ID NO:9. It is within the skill of one in the art to produce other soluble forms of canine CD23 using known proteases, such as for example by digestion of CD23 proteins with the protease papain, for 5 hours at 37° C., in 20 mM Phosphate buffer, pH 6.2.

Another embodiment is a canine CD23 protein that comprises a putative C-type lectin (long form) domain, i.e. IgE binding domain. A preferred fragment of a canine CD23 protein that includes the putative C-type lectin domain extends from about residue 162 to about residue 284 of SEQ ID NO:2, and is referred to as PCaCD23$_{123}$, which has an amino acid sequence designated SEQ ID NO:25. The size of the C-type lectin domain in the canine CD23 can vary and can be determined by one of skill in the art, using known methods, for example, random or targeted mutagenesis or structure analysis using different antibodies that bind to the C-type lectin domain and other regions of CD23. The nucleic acid molecule that encodes PCaCD23$_{123}$ corresponds to a region from about nucleotide 484 to about nucleotide 852 of SEQ ID NO:4, and is designated SEQ ID NO:24, and its complement is designated SEQ ID NO:26. The nucleic acid molecule consisting of SEQ ID NO:24 and SEQ ID NO:26 is designated nCaCD23$_{369}$.

In another embodiment, a CD23 nucleic acid molecule can be an allelic variant that includes a similar but not identical sequence to SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24 and/or SEQ ID NO:26, or any other CD23 nucleic acid sequence cited herein. For example, an allelic variant of a canine CD23 gene or nucleic acid molecule including SEQ ID NO:1 is a gene or nucleic acid molecule that occurs at essentially the same locus, or loci, in the genome as the gene including SEQ ID NO:1, but which, due to natural variations caused by, for example, mutation, alternative splicing, recombination, has a similar but not identical sequence. Because natural selection typically selects against alterations that affect function, allelic variants, e.g. alleles corresponding to, or of, cited nucleic acid sequences, usually encode proteins having similar activity to that of the protein encoded by the gene to which they are being compared. Allelic variants of genes or nucleic acid molecules can also comprise alterations in the 5' or 3' untranslated regions of the gene, e.g. in regulatory control regions, or can involve alternative splicing of a nascent transcript, thereby bringing alternative exons into juxtaposition. Allelic variants are well known to those skilled in the art and would be expected to occur naturally within a canid, since the genome is diploid, and sexual reproduction will result in the reassortment of alleles.

In one embodiment of the present invention, isolated CD23 proteins are encoded by nucleic acid molecules that hybridize under stringent hybridization conditions to the non-coding strand of nucleic acid molecules encoding canine CD23 proteins. The minimal size of a CD23 protein of the present invention is a size sufficient to be encoded by a nucleic acid molecule capable of forming a stable hybrid, i.e., hybridizing under stringent hybridization conditions, with the complementary sequence of a nucleic acid molecule encoding the corresponding natural protein. The size of a nucleic acid molecule encoding such a protein is dependent on the nucleic acid composition and the percent homology between the CD23 nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered, i.e. localized, in distinct regions on a given nucleic acid molecule.

The minimal size of a nucleic acid molecule capable of forming a stable hybrid with a nucleic acid molecules encoding a canine CD23 protein is typically at least about 12 to about 15 nucleotides in length if the nucleic acid molecule is GC-rich and at least about 15 to about 18 bases if it is AT-rich.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual,* Cold Spring Harbor Labs Press, and Meinkoth, et al., 1984, *Anal. Biochem.* 138, 267–284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as form amide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° \text{ C.} + 16.6 \log M + 0.41(\%G+C) - 500/n - 0.61(\%\text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% base pair mismatch, i.e., about 70% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization reaction solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 10% pair mismatch with a canine nucleic acid molecule of about 150 bp in length or greater, the following conditions could preferably be used. The average G+C content of canine DNA is about 52.68%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and 88.2 gram sodium citrate in 1 liter of water, pH 7) to obtain the desired concentration of SSC. The skilled artisan would calculate the washing conditions required to allow up to 10% base pair mismatch. For example, in a wash solution comprising 1×SSC and 0% formamide, the $T_m$ of perfect hybrids would be about 82° C.

$$81.5° \text{ C.} + 16.6 \log(0.15M) + (0.41 \times 52.68) - (500/150) - (0.61 \times 0) = 85.6° \text{ C.}$$

Thus, to achieve hybridization with nucleic acid molecules having about 10% base pair mismatch, hybridization washes would be carried out at a temperature of less than or equal to 75.6° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 10% base pair mismatch will not vary significantly from 75.6° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™, available from Genetics Computer Group, Madison, Wis., DNAsis™, available from Hitachi Software, San Bruno, Calif., and MacVector™, available from the Eastman Kodak Company, New Haven, Conn. A preferred method to determine percent identity among amino acid sequences and also among nucleic acid sequences includes using the GAP program with pair-wise comparisons within the program GCG™ Version 9.0-UNIX, hereinafter referred to as default parameters.

A preferred canine CD23 protein includes a protein encoded by a nucleic acid molecule of length equal to or greater than 150 nucleotides that hybridizes under conditions which preferably allow for less than or equal to about a 10% base pair mismatch, and even more preferably under conditions which allow for less than or equal to about a 5% base pair mismatch with a nucleic acid molecule selected from the group consisting of SEQ ID NO:3, SEQ ID NO:6, SEQ ID NO:9, SEQ ID NO:12, SEQ ID NO:15, SEQ ID NO:18, SEQ ID NO:21, and/or SEQ ID NO:26, or a fragment thereof having at least about 47 nucleotides.

Another preferred canine CD23 protein of the present invention includes a protein that is encoded by a nucleic acid molecule that is preferably about 90% identical, more preferably about 92%, more preferably 94%, more preferably 96%, and even more preferably about 98% identical to a nucleic acid molecule having the nucleic acid sequence SEQ ID NO:1, SEQ ID NO:4, SEQ ID NO:7, SEQ ID NO:10, SEQ ID NO:13, SEQ ID NO:16, SEQ ID NO:19, and/or SEQ ID NO:24; also preferred are fragments, i.e. portions, of such proteins encoded by nucleic acid molecules that are at least about 47 nucleotides. Percent identity as used herein is determined using the Compare function by maximum matching within the program GCG™ Version 2.1 using default parameters.

A preferred isolated protein of the present invention is a protein encoded by at least one of the following nucleic acid molecules: $nCaCD23_{2851}$, $nCaCD23_{876}$, $nCaCD23_{369}$, $nCaCD23_{384}$, $nCaCD23_{417}$, $nCaCD23_{423}$, $nCaCD23_{561}$, $nCaCD23_{624}$, or a variants of any of these nucleic acid molecules. As such, a preferred isolated protein is encoded by a nucleic acid molecule having nucleic acid sequence SEQ ID NO:1, SEQ ID NO:4, SEQ ID NO:7, SEQ ID NO:10, SEQ ID NO:13, SEQ ID NO:16, SEQ ID NO:19, and/or SEQ ID NO:24 or a protein encoded by an allelic variant of any of these listed nucleic acid molecules.

In one embodiment, a preferred protein of the present invention includes a protein that is preferably at least about 70%, more preferably at least about 75%, more preferably at least about 80%, more preferably at least about 85%, even more preferably at least about 90%, even more preferably at least about 95%, and even more preferably about 100% identical to $PCaCD23_{292}$, $PCaCD23_{123}$, $PCaCD231_{28}$, $PCaCD23_{139}$, $PCaCD23_{141}$, $PCaCD23_{187}$, and/or $PCaCD23_{208}$. Additionally preferred are proteins encoded by allelic variants of a nucleic acid molecule encoding proteins $PCaCD23_{292}$, $PCaCD23_{123}$, $PCaCD23_{128}$, $PCaCD23_{139}$, $PCaCD23_{141}$, $PCaCD23_{187}$, and/or $PCaCD23_{208}$. Also preferred are fragments thereof having at least about 80 amino acid residues.

As such, preferred CD23 proteins of the present invention include proteins having amino acid sequences that are preferably at least about 70%, preferably at least about 75%, preferably at least about 80%, more preferably at least about 85%, even more preferably at least about 90%, even more preferably at least about 95%, and even more preferably about 100% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, and/or SEQ ID NO:25. Even more preferred are CD23 proteins comprising an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20 and/or SEQ ID NO:25; and CD23 proteins encoded by allelic variants of nucleic acid molecules encoding CD23 proteins having amino acid sequences selected from the group consisting of SEQ ID NO:2, SEQ ID NO:5, SEQ ID NO:8, SEQ ID NO:11, SEQ ID NO:14, SEQ ID NO:17, SEQ ID NO:20 and/or SEQ ID NO:25.

In one embodiment of the present invention, canine CD23 proteins comprise amino acid sequence SEQ ID NO:2, SEQ ID NO:5, SEQ ID NO:8, SEQ ID NO:11, SEQ ID NO:14, SEQ ID NO:17, SEQ ID NO:20, SEQ ID NO:25, including, but not limited to, the proteins consisting the cited amino acid sequences, fusion proteins and multivalent proteins, and proteins encoded by allelic variants of nucleic acid molecules encoding proteins having amino acid sequence SEQ ID NO:2, SEQ ID NO:5, SEQ ID NO:8, SEQ ID NO:11, SEQ ID NO:14, SEQ ID NO:17, SEQ ID NO:20, SEQ ID NO:25.

In one embodiment, a preferred canine CD23 protein comprises an amino acid sequence of at least about 80 amino acids, or at least about 100 amino acids, or at least about 120 amino acids, or at least about 140 amino acids, or at least about 160 amino acids, or at least about 180 amino acids, or at least about 200 amino acids, or at least about 220 amino acids, or at least about 240 amino acids, or at least ab out 280 amino acids, or at least about 290 amino acids. In another embodiment, preferred canine CD23 proteins comprise full-length proteins, i.e., proteins encoded by full-length coding regions.

In another embodiment, a preferred canine CD23 protein comprises of an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:25, and/or a fragment thereof, such that the protein is capable of binding to IgE, CD21, CD11b, and/or CD11c; and a protein encoded by an allelic variant of a nucleic acid molecule which encodes any such protein. For a protein to be capable of binding to its ligand(s) or receptor(s), such as IgE, CD21, CD11b or CD11c, the protein must have a functional binding domain. A functional binding domain is at least the smallest piece, or fragment, of the protein that is necessary to allow binding to a ligand or receptor. For example, a functional binding domain also includes proteins that are larger than the smallest fragment necessary to allow binding to a ligand or receptor.

One of skill in the art will understand that a DNA or protein fragment of the present invention is an example of a homolog that includes a portion of a larger nucleic acid molecule or protein, respectively, of the present invention. One of skill in the art will also understand that fragments including one or more of the functional domains of CD23 and/or soluble CD23 can vary and extend beyond those particular nucleic acid or amino acid regions defined herein. Such active domains can vary in length by 1 amino acid to about 200 amino acids. Nucleic acids or amino acids essential to an active domain can be identified using standard protein or DNA binding assays known to those of skill in the art to determine the ability of an active domain to bind to its ligand(s), e.g. IgE, or to its receptor(s), e.g. CD21, CD11b, and/or CD11c.

In one embodiment, preferred CD23 proteins of the present invention are encoded by nucleic acid molecules comprising apparently full-length CD23 coding regions, i.e., nucleic acid molecules encoding an apparently full-length CD23 protein. Another embodiment of a preferred CD23 protein is a fragment thereof encoded by a nucleic acid molecule encoding a protein that includes the IgE binding site, e.g. a nucleic acid molecule encoding $PCaCD23_{123}$.

In one embodiment, a preferred CD23 protein of the present invention is encoded by a nucleic acid molecule comprising at least about 47 nucleotides, at least about 60 nucleotides, at least about 80 nucleotides, at least about 100 nucleotides, at least about 150 nucleotides, at least about 350 nucleotides, at least about 450 nucleotides, at least about 550 nucleotides, at least about 650 nucleotides, at least about 750 nucleotides, at least about 850 nucleotides, or at least about 876 nucleotides. Within this embodiment is a CD23 protein encoded by at least a portion of $nCaCD23_{2851}$ or $nCaCD23_{876}$, or by an allelic variant of either of these nucleic acid molecules.

Preferred canine CD23 proteins of the present invention are compounds that can be used to develop regulatory compounds including inhibitors and activators that, when administered to a canid in an effective manner, are capable of protecting that canid from disease mediated by CD23. Preferred regulatory compounds derived from the present invention include inhibitors and activators. In accordance with the present invention, the ability of a regulatory compound, including an inhibitor or activator, of the present invention to protect a canid from disease mediated by CD23 refers to the ability of that protein to, for example, treat, ameliorate or prevent a disease mediated by CD23 in that canid.

A disease mediated, e.g. controlled, regulated, by CD23 can include a disease mediated by IgE. IgE is an important molecule in the establishment and progression of allergic disease in an animal. IgE mediates allergy related disease, for example atopic dermatitis, asthma, inflammation, hay fever, and food sensitivities. The presence of IgE or elevated levels of IgE in a canid is indicative of such a disease. Without being bound by theory, regulation of the levels of CD23 in a canid may have the following effects upon IgE levels: (a) reducing the amount and/or activity of soluble CD23 can reduce soluble CD23's ability to bind to its receptors, for example CD21, on B cells, thereby inhibiting, preventing or reducing the ability of the soluble CD23 from generating a signal within the B cell, which would otherwise result in the production of IgE; and (b) activating membrane-bound CD23 on B cells can cause the membrane-bound CD23 to generate a signal within the B cell that reduces production of IgE by that B cell. The term, signal, or signal transduction, refers to a chemical reaction that is produced internally by a cell in response to activation of its receptor(s); activation being caused by, for example, binding of ligand to the receptor. This internal chemical reaction can lead to production of cellular molecules that can modify transcription of cellular genes. An additional beneficial effect of regulating levels or activity of CD23 in a canid is to regulate the activity of inflammatory cells by inhibiting, preventing or reducing the binding of soluble CD23 to receptor on inflammatory cells, including CD11b and CD11c, thereby inhibiting, preventing and/or reducing generation of a signal within the inflammatory cells that would otherwise result in the production of proinflammatory cytokines, e.g. interleukin-1 alpha, interleukin-1 beta, interleukin-6, or tumor necrosis factor. Another beneficial effect of regulating the activity or levels of CD23 in a canid includes inhibition of IgE-mediated antigen presentation (IgE-MAP). Without being bound by theory, IgE-MAP is believed to be responsible for enhancing the immune response to an antigen by the following mechanism: an IgE-antigen complex binds to membrane-bound CD23 on antigen presenting cells causing enhanced internalization of the antigen. This antigen is then presented to T cells, and an immune response, often a Th2-type response, is generated. Inhibition of the activity of membrane-bound CD23 on antigen presentation cells could reduce IgE-MAP.

One embodiment of a canine CD23 protein of the present invention is a fusion protein that includes a canine CD23 protein-containing domain attached to one or more fusion segments. Suitable fusion segments for use with the present invention include, but are not limited to, segments that can: enhance a protein's stability; act as an immunopotentiator to enhance an immune response against canine CD23 protein; and/or assist in purification of a canine CD23, e.g., by affinity chromatography. A suitable fusion segment can be a domain of any size that has the desired function, e.g., imparts increased stability, imparts increased immunogenicity to a protein, and/or simplifies purification of a protein. Fusion segments can be joined to amino and/or carboxyl termini of the CD23 containing domain of the protein and can be susceptible to cleavage in order to enable straightforward recovery of a CD23 protein. Fusion proteins are preferably produced by culturing a recombinant cell transformed with a fusion nucleic acid molecule that encodes a protein including the fusion segment attached to either the carboxyl and/or amino terminal end of a CD23 containing domain. Preferred fusion segments include a metal binding domain, e.g., a poly-histidine segment; an immunoglobulin binding domain, e.g., Protein A, Protein G, T cell, B cell, Fc receptor or complement protein antibody-binding domains; a sugar binding domain, e.g., a maltose binding domain;

and/or a tag domain, e.g., at least a portion of β-galactosidase, a strep tag peptide, a T7 tag peptide, a Flag™ peptide, or other domains that can be purified using compounds that bind to the domain, such as monoclonal antibodies. More preferred fusion segments include metal binding domains, such as a poly-histidine segment; a maltose binding domain; a strep tag peptide, such as that available from Biometra in Tampa, Fla.; and an S10 peptide. One embodiment of a fusion protein is a chimera of CD23 or soluble CD23 with a functional moiety. This moiety can, for example, have the function of allowing oligomerization of the chimeric CD23 proteins.

The present invention also includes mimetopes of canine CD23 proteins of the present invention. As used herein, a mimetope of a canine CD23 protein of the present invention refers to any compound that is able to mimic the activity of such a canine CD23 protein, often because the mimetope has a structure that mimics the particular canine CD23 protein. Mimetopes can be, but are not limited to: peptides that have been modified to decrease their susceptibility to degradation such as all-D retro peptides; anti-idiotypic and/or catalytic antibodies, or fragments thereof, non-proteinaceous immunogenic portions of an isolated protein, e.g., carbohydrate structures; and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a canine CD23 nucleic acid molecule. A nucleic acid molecule of the present invention can include an isolated natural canine CD23 gene, cDNA, or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid, i.e., hybridization under stringent hybridization conditions, with the complementary sequence of another nucleic acid molecule.

In accordance with the present invention, an isolated nucleic acid molecule is a nucleic acid molecule that has been removed from its natural milieu, i.e., that has been subjected to human manipulation, and can include DNA, RNA, or derivatives of either DNA or RNA. As such, the term isolated does not reflect the extent to which the nucleic acid molecule has been purified. Isolated canine CD23 nucleic acid molecules of the present invention, including natural sequences and homologs thereof, can be isolated from a natural source or produced using recombinant DNA technology, e.g., polymerase chain reaction (PCR) amplification or cloning, or chemical synthesis. Isolated canine CD23 nucleic acid molecule homologs, can include, for example, natural allelic variants and nucleic acid molecules modified by nucleotide insertions, deletions, substitutions, and/or inversions in a manner such that the modifications do not substantially interfere with the nucleic acid molecule's ability to encode a canine CD23 protein of the present invention.

A canine CD23 nucleic acid molecule homolog can be produced using a number of methods known to those skilled in the art, see, for example, Sambrook et al., ibid. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to build a mixture of nucleic acid molecules, and combinations thereof. Nucleic acid molecule homologs can be selected by hybridization with canine CD23 nucleic acid molecules or by screening the function of a protein encoded by the nucleic acid molecule, e.g., ability to elicit an immune response against at least one epitope of a canine CD23 protein or ability to mimic one or more of canine CD23 protein activity or function.

An isolated nucleic acid molecule of the present invention can include a nucleic acid sequence that encodes at least one canine CD23 protein of the present invention, examples of such proteins being disclosed herein. Although the phrase, nucleic acid molecule, primarily refers to the physical nucleic acid molecule and the phrase, nucleic acid sequence, primarily refers to the sequence of nucleotides on the nucleic acid molecule, the two phrases can be used interchangeably, especially with respect to a nucleic acid molecule, or a nucleic acid sequence, being capable of encoding a canine CD23 protein.

A preferred nucleic acid molecule of the present invention, when administered to an animal, is capable of protecting that animal from a disease mediated by CD23. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, e.g., an canine CD23 protein of the present invention, the nucleic acid molecule being delivered to the animal, for example, by direct injection, i.e., as a genetic vaccine, or in a vehicle such as a recombinant virus vaccine or a recombinant cell vaccine.

In one embodiment of the present invention, a preferred canine CD23 nucleic acid molecule includes an isolated nucleic acid molecule which hybridizes under conditions which allow less than or equal to about 10% base pair mismatch, and even more preferably under conditions which allow less than or equal to about 5% base pair mismatch with a nucleic acid molecule selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26, and/or a fragment thereof having at least 47 nucleotides.

One embodiment of the present invention includes a nucleic acid molecule of at least 150 nucleotides that hybridizes, in a solution comprising 1×SSC and 0% formamide, at a temperature of about 75.6° C., to an isolated nucleic acid molecule selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26, as well as fragments thereof that are at least 47 nucleotides in length. Also included are other nucleic acid molecules that hybridize, in a solution comprising 1×SSC and 0% foramide, at a temperature of about 75.6° C., to an isolated nucleic acid molecule selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26 wherein said nucleic acid molecule comprises at least about 47 nucleotides.

Preferred canine CD23 nucleic acid molecules of the present invention include nucleic acid molecules comprising a nucleic acid sequence that is preferably at least about 90%, more preferably at least about 92%, more preferably about 94%, more preferably about 96%, and even more preferably at least about 98% identical to a nucleic acid sequence selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26. Also preferred are oligonucleotides of any of such nucleic acid molecules, particularly those that are at least about 47 nucleotides. Percent identity may be determined using the program GCG™ Version 9.0-UNIX using default parameters.

One embodiment of the present invention is a nucleic acid molecule comprising all or part of nucleic acid molecules $nCaCD23_{2851}$, $nCaCD23_{876}$, $nCaCD23_{369}$, $nCaCD23_{384}$, $nCaCD23_{417}$, $nCaCD23_{423}$, $nCaCD23_{561}$, and $nCaCD23_{624}$, or allelic variants of these nucleic acid molecules. As such, a preferred nucleic acid molecule of the present invention includes at least a portion of nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and/or SEQ ID NO:26, as well as allelic variants of nucleic acid molecules having these nucleic acid sequences. Also included in the present invention are other homologs of nucleic acid molecules having these nucleic acid sequences; preferably such a homolog encodes or is complementary to a nucleic acid molecule that encodes at least one epitope that elicits an immune response against a protein having amino acid sequence SEQ ID NO:2. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound, such as a multivalent vaccine.

In one embodiment, a CD23 nucleic acid molecule of the present invention encodes a protein that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to $PCaCD23_{292}$, $PCaCD23_{123}$, $PCaCD23_{128}$, $PCaCD23_{139}$, $PCaCD23_{141}$, $PCaCD23_{187}$, and $PCaCD23_{208}$.

In one embodiment, a canine CD23 nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:2, SEQ ID NO:5, SEQ ID NO:8, SEQ ID NO:11, SEQ ID NO:14, SEQ ID NO:17, SEQ ID NO:20, and/or SEQ ID NO:25. The present invention also includes a canine nucleic acid molecule encoding a protein having at least a portion of SEQ ID NO:2, SEQ ID NO:5, SEQ ID NO:8, SEQ ID NO:11, SEQ ID NO:14, SEQ ID NO:17, SEQ ID NO:20, and/or SEQ ID NO:25, as well as allelic variants of a canine CD23 nucleic acid molecule encoding a protein having these sequences, including nucleic acid molecules that have been modified to accommodate codon usage properties of the cells in which such nucleic acid molecules are to be expressed.

In another embodiment, a preferred canine CD23 nucleic acid molecule encodes a CD23 protein at least about 80 amino acids, at least about 100 amino acids, at least about 120 amino acids, at least about 150 amino acids, at least about 170 amino acids, at least about 190 amino acids, at least about 210 amino acids in length, at least about 230 amino acids in length, at least about 250 amino acids in length, or about 292 amino acids in length.

A preferred canine CD23 nucleic acid molecule comprises a nucleic acid sequence that encodes at least a portion of a canine CD23 protein that is capable of binding to CD23's ligand(s) or receptor(s) as disclosed herein. Preferably, such a nucleic acid molecule encodes a protein having SEQ ID NO:2, SEQ ID NO:5, SEQ ID NO:8, SEQ ID NO:11, SEQ ID NO:14, SEQ ID NO:17, SEQ ID NO:20 and/or SEQ ID NO:25, or allelic variants thereof.

In one embodiment, there is an isolated nucleic acid molecule which can be selected from the group consisting of: (a) a nucleic acid molecule comprising a nucleic acid sequence selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:24, and SEQ ID NO:26; and (b) a nucleic acid molecule comprising an at least 30 nucleotide portion identical in sequence to a consecutive 30 nucleotide portion of a sequence as set forth in (a).

In one embodiment, preferred canine CD23 nucleic acid molecule of the present invention comprises an apparently full-length CD23 coding region, i.e., the preferred nucleic acid molecule encodes an apparently full-length CD23 protein.

Knowing the nucleic acid sequences of certain canine CD23 nucleic acid molecules of the present invention allows one skilled in the art to, for example, (a) make copies of those nucleic acid molecules, (b) obtain nucleic acid molecules including at least a portion of such nucleic acid molecules, e.g., nucleic acid molecules including full-length genes, full-length coding regions, regulatory control sequences, truncated coding regions, and (c) obtain other canine CD23 nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. A preferred library to screen or from which to amplify nucleic acid molecules is a canine peripheral blood mononuclear cell library. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising canine CD23 nucleic acid molecules or other canine CD23 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of from about 100 to about 200 nucleotides. The present invention includes oligonucleotides that can be used as, for example, probes to identify nucleic acid molecules, primers to produce nucleic acid molecules, or therapeutic reagents to inhibit canine CD23 protein production or activity, e.g., as antisense-, triplex formation-, ribozyme- and/or RNA drug-based reagents. The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of canine CD23 nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the nucleic acid molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function, i.e., direct gene expression, in recombinant cells of the present invention, including in bacterial, fungal, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, or insect and mammalian cells, such as, but not limited to, tac, lac, trp, trc, oxy-pro, omp/lpp, rrnB, bacteriophage lambda, such as lambda $P_L$ and lambda $P_R$ and fusions that include such promoters, bacteriophage T7, T7lac, bacteriophage T3, bacteriophage SP6, bacteriophage SP1, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus, such as immediate early promoter, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters, e.g., promoters inducible by interferons or interleukins.

Suitable and preferred nucleic acid molecules to include in recombinant vectors of the present invention are as disclosed herein. Particularly preferred nucleic acid molecules to include in recombinant vectors, and particularly in recombinant molecules, include $nCaCD23_{2851}$, $nCaCD23_{876}$, $nCaCD23_{369}$, $nCaCD23_{384}$, $nCaCD23_{4,7}$, nCaCD23 $nCaCD23_{561}$, and $nCaCD23_{624}$.

Recombinant molecules of the present invention may also (a) contain secretory signals, i.e., signal segment nucleic acid sequences, to enable an expressed CD23 protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/ or within the nucleic acid sequences of nucleic acid molecules of the present invention.

Another embodiment of the present invention includes a recombinant cell comprising a host cell transformed with one or more nucleic acid molecules or recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed, i.e., recombinant, cell in such a manner that their ability to be expressed is retained. Preferred nucleic acid molecules with which to transform a cell include canine CD23 nucleic acid molecules disclosed herein. Particularly preferred nucleic acid molecules with which to transform a cell include $nCaCD23_{2851}$, $nCaCD23_{876}$, $nCaCD23_{369}$, $nCaCD23_{384}$, $nCaCD23_{417}$, nCaCD23423, $nCaCD23_{561}$, and $nCaCD23_{624}$.

Suitable host cells to transform include any cell that can be transformed with a nucleic acid molecule of the present invention. Host cells can be either untransformed cells or cells that are already transformed with at least one nucleic acid molecule, e.g., nucleic acid molecules encoding one or more proteins of the present invention and/or other proteins. Host cells of the present invention either can be endogenously, i.e., naturally, capable of producing canine CD23 proteins of the present invention or can be capable of producing such proteins after being transformed with at least one nucleic acid molecule of the present invention. Host cells of the present invention can be any cell capable of producing at least one protein of the present invention, and include bacterial, fungal, including yeast, insect, and other animal and plant cells. Preferred host cells include bacterial, mycobacterial, yeast, insect and mammalian cells. More preferred host cells include Salmonella, Escherichia, Bacillus, Listeria, Saccharomyces, Pichia, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-$1_x$3987 and SR-$11_x$4072; Pichia; *Spodoptera frugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines, e.g., human, murine or chicken embryo fibroblast cell lines, myeloma cell lines, Chinese hamster ovary cells, mouse NIH/3T3 cells, LMTK[31] cells and/or HeLa cells. In one embodiment, the proteins may be expressed as heterologous proteins in myeloma cell lines employing immunoglobulin promoters.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

Recombinant cells of the present invention can also be co-transformed with one or more recombinant molecules including CD23 nucleic acid molecules encoding one or more proteins of the present invention and one or more other nucleic acid molecules encoding other compounds.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals, e.g., promoters, operators, enhancers, substitutions or modifications of translational control signals, e.g., ribosome binding sites, Shine-Dalgarno sequences, modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated canine CD23 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a canine CD23 protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase recovering the protein, as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in substantially pure form. As used herein, substantially pure refers to a purity that allows for the effective use of the protein as a therapeutic composition or diagnostic. A therapeutic composition for animals, for example, should exhibit no substantial toxicity.

The present invention also includes isolated, i.e., removed from their natural milieu, antibodies that selectively bind to a canine CD23 protein of the present invention or a mimetope thereof, e.g., anti-canine CD23 antibodies. As used herein, the term selectively binds to an CD23 protein refers to the ability of antibodies of the present invention to preferentially bind to specified proteins and mimetopes thereof of the present invention. Binding can be measured using a variety of methods standard in the art including enzyme immunoassays, e.g., ELISA, immunoblot assays, etc.; see, for example, Sambrook et al., ibid., and Harlow, et al., 1988, *Antibodies, a Laboratory Manual,* Cold Spring Harbor Labs Press; Harlow et al., ibid., is incorporated herein by reference in its entirety. An anti-CD23 antibody of the present invention preferably selectively binds to a canine CD23 protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope of the present invention to produce the antibodies and (b) recovering the antibodies. In another method, antibodies of the present invention are produced recombinantly using techniques as heretofore disclosed to produce CD23 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from effects mediated by canine CD23 by such antibodies and/or (b) as tools to screen expression libraries and/or to recover desired proteins of the present invention from a mixture of proteins and other contaminants. Furthermore, antibodies of the present invention can be used to target cytotoxic agents to canine CD23 and cells containing canine CD23 on the cell surface. Targeting can be accomplished by conjugating, i.e., stably joining, such antibodies to the cytotoxic agents using techniques known to those skilled in the art. Suitable cytotoxic agents are known to those skilled in the art. Furthermore, antibodies of the present invention can be used to detect CD23 in a putative CD23 containing biological sample, by contacting the putative CD23 containing biological sample with anti-CD23 antibodies under conditions suitable for formation of a CD23-antibody complex, and then detecting said complex. Methods to detect said method are known to those skilled in the art and are contained herein.

One embodiment of the present invention is a therapeutic composition that, when administered to a canid in an effective manner, is capable of protecting that animal from a disease mediated by canine CD23, such as for example allergy or inflammation. Therapeutic compositions of the present invention include compounds that are capable of regulating CD23 amounts and/or activity. A compound capable of regulating CD23 amounts and/or activity may work by associating, interacting, binding to, and/or modifying CD23, CD23 ligands, such as for example IgE, and CD23 receptors, such as for example CD21, CD11b, and/or CD11c. Examples of regulatory compounds derived from CD23 proteins of the present invention include an isolated antibody that selectively binds to a canine CD23 protein or other inhibitors or activators of CD23 protein activity or amount. As such, these regulatory compounds may include antibodies, peptides, substrate analogs, and other large or small molecules which can be organic or inorganic. As used herein, a protective compound refers to a compound, that when administered to an animal in an effective manner, is able to treat, ameliorate, and/or prevent a disease mediated by CD23.

One embodiment of the present invention is a therapeutic composition that, when administered to a canid, reduces allergy or inflammation present in said canid, said therapeutic composition comprising an excipient and a compound derived from a protein selected from the group consisting of: (a) a protein comprising an amino acid sequence that is at least 70% homologous to an amino acid sequence selected from the group consisting of SEQ ID NO:5, SEQ ID NO:8, SEQ ID NO:11, SEQ ID NO:14, SEQ ID NO:17, SEQ ID NO:20 and SEQ ID NO:25, (b) a protein comprising an amino acid sequence from the group consisting of SEQ ID NO:5, SEQ ID NO:8, SEQ ID NO:11, SEQ ID NO:14, SEQ ID NO:17, SEQ ID NO:20 and SEQ ID NO:25, wherein said protein is at least about 80 amino acids in length; (c) a protein comprising a fragment of (a) or (b), wherein said fragment is capable of binding to a protein selected from the group consisting of IgE, CD11b, CD11c, and CD21, or (d) a protein encoded by an allelic variant of a nucleic acid molecule that encodes any protein of (a), (b), or (c). Therapeutic compositions of the present invention include a regulatory compound.

As used herein, the term derived, or derived from, refers to a peptide, antibody, mimetope, nucleic acid molecule, or other compound that was obtained from a CD23 protein or nucleic acid molecule of the present invention. Methods to obtain derivatives from a CD23 molecule of the present invention are known in the art, and as such include, but are not limited to, molecular modeling of CD23 to determine active sites, i.e. sites that interact with other molecules, such as receptors or ligands, and predicting from these active sites smaller fragments and/or mimetopes that retain and/or mimic these active sites, thereby inhibiting or activating CD23 activity; screening of peptide or small chemical compound libraries against CD23 proteins of the present invention; and screening of polyclonal or monoclonal antibodies to find antibodies that specifically bind CD23 proteins of the present invention.

A CD23 inhibitor of the present invention is identified by its ability to bind to, modify, or otherwise interact with, a CD23 protein, thereby inhibiting the activity of CD23. Suitable inhibitors of CD23 activity are compounds that inhibit CD23 protein activity in at least one of a variety of ways: (1) by binding to or otherwise interacting with or otherwise modifying the CD23 IgE binding, i.e. ligand binding, site, (2) by interacting with other regions of the CD23 protein to inhibit CD23 activity, for example, by allosteric interaction, (3) by binding to or otherwise interacting with or otherwise modifying a CD23 receptor binding site such that CD23 is less likely to bind to the CD23 receptor binding site, and (4) by inhibiting the processing, for example proteolytic processing, of CD23 into different forms of CD23, thereby decreasing the amount of soluble CD23 available for binding to receptors of CD23; such a compound is termed a proteolysis inhibitor. Inhibitors of CD23 are preferably relatively small compounds.

A CD23 activator of the present invention is identified by its ability to bind to, modify, or otherwise interact with, a CD23 protein, thereby increasing the activity of CD23. Suitable activators of CD23 activity are compounds that activate CD23 protein activity, for example, (1) by binding to, or otherwise interacting with, or otherwise modifying the CD23 IgE binding site, (2) by interacting with other regions of the CD23 protein to increase CD23 activity, for example, by allosteric interaction, and (3) by binding to, or otherwise interacting with, or otherwise modifying a CD23 receptor binding site. Activators of CD23 are preferably relatively small compounds.

Preferred CD23 regulatory compounds of the present invention include, but are not limited to, CD23 substrate analogs. A CD23 substrate analog refers to a compound that interacts with, e.g., binds to, associates with, and/or modifies, an active site of a CD23 protein. An active site of a CD23 protein refers to at least a portion of a CD23 protein that selectively binds to a CD23 binding partner, such as a CD23 receptor or CD23 ligand. The term CD23 binding partner refers to a chemical group or molecule in the outer cell membrane or in the cell interior that has an affinity for CD23, such that CD23 selectively binds to the binding partner. Examples of CD23 receptors include CD21, CD11b, and CD11c. An example of a CD23 ligand is IgE. A CD23 substrate analog can be of any inorganic or organic composition. A CD23 substrate analog can be, but need not be, structurally similar to a CD23 natural substrate as long as the analog can interact with the active site of that CD23 protein or its binding partners. A CD23 substrate analog can include molecules that bind to a CD23 allosteric site, in such a manner that CD23 activity of the CD23 is regulated, inhibited or activated. A CD23 substrate analog can be designed using computer-generated structures of CD23 proteins of the present invention or computer structures of CD23 natural ligands or receptors. Preferred sites to model include one or more of the active sites of a CD23 protein of the present invention. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, e.g., CD23, IgE, CD21, CD11b, or CD11c. A preferred CD23 substrate analog is a CD23 mimetic compound, i.e., a compound that is structurally and/or functionally similar to a natural substrate of a CD23 of the present invention, particularly to the region of the substrate that interacts with the CD23 active site, but that inhibits or activates CD23 activity upon interacting with the CD23 active site.

The present invention also includes a therapeutic composition comprising at least one CD23-derived compound of the present invention in combination with at least one additional compound protective against allergy or inflammation. Examples of such protective compounds include anti-inflammatory steroids, antihistamines, and anti-IgE antibodies.

In one embodiment, a therapeutic composition of the present invention can be used to protect an animal from a disease mediated by CD23 by administering such composition to a canid in order to prevent undesirable CD23 levels. Such administration can include, but is not limited to, oral, intravenous, intramuscular, intra ocular, mucosal, intranasal, subcutaneous, or transdermal application. A preferred route of administration is subcutaneous. In order to protect an animal from a disease mediated by CD23, a therapeutic composition of the present invention is administered to the animal in an effective manner such that the composition is capable of protecting that animal from a disease mediated by CD23. Therapeutic compositions of the present invention can be administered to animals prior to disease in order to prevent disease and/or can be administered to animals after disease occurs. The exact dose, administration regimen, and administration route of therapeutic compositions of the present invention can be determined by one skilled in the art.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphercs, and transdermal delivery systems. Other controlled release formulations of the present invention include liquids that, upon administration to an animal, form a solid or a gel in situ. Preferred controlled release formulations are biodegradable, i.e., bioerodible.

According to one embodiment, a nucleic acid molecule of the present invention can be administered to an animal in a fashion to enable expression of that nucleic acid molecule into a protective protein or protective RNA, e.g., antisense RNA, ribozyme, triple helix forms or RNA drug, in the animal. Nucleic acid molecules can be delivered to an animal in a variety of methods including, but not limited to, (a) administering a naked, i.e., not packaged in a viral coat or cellular membrane, nucleic acid as a genetic vaccine, e.g., as naked DNA or RNA molecules, such as is taught, for example in Wolff et al., 1990, *Science* 247, 1465–1468, or (b) administering a nucleic acid molecule packaged as a recombinant virus vaccine or as a recombinant cell vaccine, i.e., the nucleic acid molecule is delivered by a viral or cellular vehicle.

A genetic, i.e., naked nucleic acid, vaccine of the present invention includes a nucleic acid molecule of the present invention and preferably includes a recombinant molecule of the present invention. A genetic vaccine of the present invention can comprise one or more nucleic acid molecules of the present invention operatively linked to a transcriptional control sequence. In one embodiment, genetic vaccines include at least a portion of a viral genome, i.e., a viral vector. Any suitable transcription control sequence can be used, including those disclosed as suitable for protein production. Particularly preferred transcription control sequences include cytomegalovirus immediate early, preferably in conjunction with Intron-A, Rous sarcoma virus long terminal repeat, and tissue-specific transcription control sequences, as well as transcription control sequences endogenous to viral vectors if viral vectors are used. The incorporation of a "strong" polyadenylation signal is also preferred. Preferred viral vectors include those based on alphaviruses, poxviruses, adenoviruses, herpesviruses, picornaviruses, and retroviruses.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient, e.g., phosphate buffered saline, alone or in a carrier, e.g., lipid-based vehicles.

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses, such as Sindbis virus, raccoon poxviruses, species-specific herpesviruses and species-specific poxviruses. An example of methods to produce and use alphavirus recombinant virus vaccines are disclosed in U.S. Pat. No. 5,766,602, Xiong et al., issued Jun. 16, 1998; U.S. Pat. No. 5,753,235, Haanes et al., issued May 19, 1998; and U.S. Pat. No. 5,804,197, Haanes et al., issued Sep. 8, 1998, all of which are incorporated by reference herein in their entirety.

When administered to an animal, a recombinant virus vaccine of the present invention infects cells within the immunized animal and directs the production of a protective protein or RNA nucleic acid molecule that is capable of protecting the animal from a disease mediated by CD23 as disclosed herein. For example, a recombinant virus vaccine comprising a canine CD23 nucleic acid molecule of the present invention is administered according to a protocol that results in the animal producing a sufficient immune response to protect itself from a disease mediated by CD23. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, E. coli, Listeria, Mycobacterium, S. frugiperda, yeast, (including Saccharomyces cerevisiae and Pichia pastoris), BHK, CV-1, myoblast G8, COS, e.g., COS-7, Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from a disease mediated by CD23 can be tested in a variety of ways including, but not limited to, detection of protective antibodies (using, for example, proteins or mimetopes of the present invention), detection of the amount of CD23, or detection of cellular immunity within the treated animal. In one embodiment, therapeutic compositions can be tested in animal models such as mice. Such techniques are known to those skilled in the art.

One embodiment of the present invention is the use of a therapeutic composition of the present invention in a method to reduce the activity and/or amount of IgE, inflammation, CD23, or IgE-MAP in a canid. A therapeutic composition of the present invention can activate CD23 present on canine B cells, thereby reducing the amount of IgE produced by the B cell, and therefore can include an activator of CD23, such as but not limited to, an antibody to CD23, a substrate analog of CD23, a small molecule activator of CD23, or any other compound derived from CD23 that functions to reduce the amount of IgE produced by a B cell.

A therapeutic composition of the present invention that reduces the amount of soluble CD23 can include a compound that would prevent proteolytic processing of CD23 to its soluble form(s), thereby preventing generation of the soluble forms of CD23. Such a compound can include a small molecule inhibitor or a soluble CD23 mimetope. A therapeutic composition that inhibits the binding of soluble CD23 to its receptor could include, for example, a small molecule inhibitor, a receptor antagonist, an antibody to soluble CD23, and a soluble CD23 mimetope. A therapeutic composition that reduces IgE-mediated antigen presentation, by inhibiting the binding of an IgE-antigen complex to CD23 on the antigen presenting cells, can include, for example, a small molecule inhibitor, a receptor antagonist, an antibody to soluble CD23, a soluble CD23 mimetope or other compound that prevents or disrupts such binding.

One embodiment of the present invention is a method to identify a compound that regulates the amount or activity of canine CD23. Such a method includes the steps of: (a) contacting, e.g. combining, mixing, an isolated canine CD23 protein with a putative regulatory compound under conditions in which, in the absence of the compound, the protein has CD23 activity, and (b) determining if the putative regulatory compound regulates CD23 activity. Such conditions under which the protein has CD23 activity include a CD23 with a correct three-dimensionally folded protein structure under physiologic conditions, i.e. physiologic pH, physiologic ionic concentrations, and physiologic temperatures. Regulatory compounds include compounds that inhibit or activate canine CD23.

Putative regulatory compounds to screen include small organic molecules, antibodies (including mimetopes thereof), substrate analogs and other compounds described herein. Methods to determine CD23 activity are known in the art, for example determining the ability of CD23 to bind to IgE. Methods to determine binding of putative regulatory compounds, or IgE, to a CD23 protein are known to those of skill in the art, and include, for example, determining changes in molecular mass using surface plasmon resonance, e.g. determining light scatter by an inhibitor of a canine CD23 protein, before and after contacting the inhibitor or protein with a CD23 protein or inhibitor, respectively; and determining changes in molecular mass by other methods, such as size exclusion chromatography; and using radiolabelled putative regulatory compounds and determining if said radiolabelled compounds bind to a CD23 protein of the present invention.

Activities of canine CD23 to regulate include (a) binding of soluble CD23 to a B cell, (b) binding of soluble CD23 to an inflammatory cell, (c) binding of IgE to CD23 on an antigen presenting cell, (d) binding of soluble CD23 to IgE on a B cell, and (e) binding of IgE to CD23 on a B cell. To determine if a compound has a regulatory effect on CD23, a number of methods exist and are known to one of skill in the art, and include (a) detecting signal transduction in a B cell; (b) detecting signal transduction in an inflammatory cell; (c) detecting enhanced internalization of an antigen in an antigen presenting cell; (d) detecting binding of CD23 to CD21, CD11b or CD11c on an inflammatory cell;(e) detecting binding of CD23 to CD21 or IgE on a B cell; (f) detecting binding of IgE to CD23 on a B cell; and (g) detecting binding of IgE to CD23 on an antigen presenting cell.

Suitable assays to detect signal transduction resulting from CD23 binding to its receptor or ligand are known in the art. For example, one embodiment would include an assay in which to detect a signal generated by CD23 binding to its ligand in which: (a) a naturally occurring or transformed B cell line expressing CD23 is established; (b) the B cells are treated with a putative activator of CD23; and (c) the presence or absence of signal transduction in the B cells is detected. Methods to detect cellular signal transduction are known to those skilled in the art, and may include detection of release of intracellular calcium, detection of proteins that increase in amount and/or activity in response to the signal, and/or measurement of phosphorylation of secondary messengers, such as phosphatidyl choline and/or phosphatidyl inositol. An inhibitor may be detected in a similar manner, for example (a) expressing functional canine CD23 on the surface of a cell; (b) contacting the cell with a putative inhibitor of CD23; (c) treating the cell with a compound that causes activation of CD23, for example, IL-4 (interleukin-4); and (d) determining the presence or absence of a signal, in the above-mentioned ways.

To detect binding of CD23 to a CD23 binding partner, a variety of methods are known to one skilled in the art. Such methods include, but are not limited to an assay in which CD23 and a CD23 binding partner can interact and/or bind to each other, using, for example, the yeast two-hybrid system, see for example, Luban, et al. 1995, *Curr. Opin. Biotechnol.*, 6, 59–64; and identifying those proteins that specifically bind to the canine CD23 protein binding domain. Additional methods to identify protein-protein interactions include Biacore® screening, confocal immunofluorescent microscopy, UV cross-linking, and immunoprecipitations. An example of a CD23 protein binding domain is an IgE-binding domain, and a protein that would bind to a CD23 IgE-binding domain would be IgE.

One embodiment of the present invention is a method to detect canine CD23 which includes the steps of: (a) contacting a putative canine CD23-containing biological sample with a molecule capable of selectively binding to canine CD23, under conditions suitable for formation of a complex between the molecule and CD23; and (b) detecting the presence of CD23 by detecting the complex. Presence of such a complex indicates that the canid is producing CD23. Molecules capable of selectively binding to canine CD23 proteins of the present invention include CD23 receptors, CD23 ligands, modified forms of CD23 ligands and/or receptors that can selectively bind to CD23, antibodies, both polyclonal and monoclonal, that specifically bind CD23, and other molecules that can selectively bind to CD23. A molecule capable of selectively binding to a canine CD23 molecule of the present invention is also referred to as a CD23 binding partner. A preferred molecule capable of selectively binding to a canine CD23 of the present invention is an anti-canine CD23 antibody.

Formation of a complex between a CD23 protein and a molecule that is capable of selectively binding to CD23 refers to the ability of a molecule to selectively bind to the CD23 in order to form a stable complex that can be detected, e.g. measured or determined. As used herein, the term, selectively binds to a CD23, refers to the ability of molecule to preferentially bind to CD23 protein, without being able to substantially bind to other proteins. A protein that is capable of selectively binding to a CD23 protein is also referred to herein as a CD23 binding protein. Binding between a molecule that selectively binds to CD23 and a CD23 protein is effected under conditions suitable to form a complex; such conditions, e.g., appropriate concentrations, buffers, temperatures, reaction times, as well as methods to optimize such conditions are known to those skilled in the art. Examples of complex formation conditions are also disclosed in, for example, in Sambrook et al., ibid.

As used herein, the term, detecting complex formation, refers to determining if any complex is formed, i.e., assaying for the presence, i.e. existence, of a complex. If complexes are formed, the amount of complexes formed can, but need not be, determined. Complex formation, or selective binding, between a molecule that selectively binds to CD23 and any CD23 in the composition can be detected using a variety of methods standard in the art, see, for example, Sambrook et al. ibid.

In one embodiment, a putative CD23-containing composition of the present method includes a biological sample from an animal. A suitable biological sample includes, but is not limited to, a bodily fluid composition or a cellular composition. A bodily fluid refers to any fluid that can be collected, i.e. obtained, from an animal, examples of which include, but are not limited to, blood, serum, plasma, urine, tears, aqueous humor, cerebrospinal fluid (CSF), saliva, lymph, nasal secretions, milk, and feces. Such a composition of the present method can, but need not be, pretreated to concentrate CD23 contained in the fluid. For example, CD23 contained in a bodily fluid can be precipitated from other proteins using different concentrations of ammonium sulfate to cause precipitation of proteins of different solubilities. A preferred composition of the present invention is blood, serum or plasma.

A complex can be produced in solution or immobilized on a substrate. Examples of methods to detect a complex include, but are not limited to, use of one or more of the following assays: an enzyme-linked immunoassay, a radioimmunoassay, a fluorescence immunoassay, a chemiluminescent assay, a lateral flow assay, an agglutination assay, a particulate-based assay, e.g., using particulates such as, but not limited to, magnetic particles or plastic polymers, such as latex or polystyrene beads, an immunoprecipitation assay, a BioCore™ assay, e.g., using colloidal gold, and an immunoblotting assay, e.g., a western blot. Such assays are well known to those skilled in the art. Assays can be used to give qualitative or quantitative results depending on how they are used. Some assays, such as agglutination, particulate separation, and immunoprecipitation, can be observed visually, e.g., either by eye or by a machine, such as a densitometer or spectrophotometer, without the need for a detectable marker. In other assays, conjugation, i.e., attachment, of a detectable marker to the CD23 molecule that selectively binds to a CD23 protein aids in detecting complex formation. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase, e.g., alkaline phosphatase, biotin, avidin, a peroxidase, e.g., horseradish peroxidase, and biotin-related compounds or avidin-related compounds, e.g., streptavidin or ImmunoPure® NeutrAvidin available from Pierce, Rockford, Ill. Methods to attach a detectable marker to a CD23 molecule of the present invention are known in the art, see for example Grieve et al., PCT publication number WO 98/12563, published Mar. 26, 1998, or Frank et al., PCT publication number WO 98/23964, published Jun. 4, 1998, both of which are incorporated by reference herein in their entireties.

One embodiment of the present invention includes a kit to test if a canid for the presence of CD23 in a canid, comprising a molecule capable of selectively binding to a canine CD23 protein, and a means for determining the presence of a complex of CD23 and said CD23 selectively binding molecule, wherein said means enables the detection of said complex, wherein detection of said complex indicates the presence of CD23 in a canid. Higher than normal levels of CD23 indicate the presence of allergy or inflammation in a canid. The kit comprises a molecule that is capable of selectively binding to a canine CD23 protein of the present invention, and as such can include a CD23 binding protein, examples of which include, but are not limited to, antibodies to CD23, CD23 receptors, modified forms of CD23 ligands and/or receptors that can selectively bind to CD23, and other proteins or other molecules that can selectively bind to CD23. A preferred molecule that selectively binds to CD23 is an antibody to CD23. The kit also comprises a means for determining susceptibility to or presence of allergy or inflammation, which comprises use of the molecule that selectively binds to the canine CD23 protein to identify susceptibility or presence of allergy or inflammation. Methods to use such a selectively binding molecule to detect another molecule are known in the art, see for example Grieve et al., PCT publication number WO 08/015,414, or Frank et al., PCT publication number WO 98/23964, both of which are incorporated by reference herein in their entireties.

The following example is provided for the purposes of illustration and is not intended to limit the scope of the present invention. The following example includes a number of recombinant DNA and protein chemistry techniques known to those skilled in the art; see, for example, Sambrook et al., ibid.

EXAMPLE 1

This example describes the isolation and sequencing of certain canine CD23 nucleic acid molecules of the present invention.

This example describes the use of mouse synthetic oligonucleotide PCR primers to isolate a mouse CD23 nucleic acid fragment, then using the mouse CD23 fragment as a template to generate a probe to isolate a canine CD23 nucleic acid molecule from a canine cDNA library. This approach was undertaken because mouse PCR primers alone were unable to pull out a canine CD23 nucleic acid molecule.

Synthetic oligonucleotide primers were designed based on the nucleic acid sequence of the mouse CD23 gene (GenBank Accession Number x64223) and used to isolate a nucleic acid molecule encoding mouse CD23 as follows. Sense primer mCD23/+143, having the sequence 5'-GGGAAACGGA GAAGAATCTA A AAC-3', designated SEQ ID NO:22, was used in combination with antisense primer mCD23/-965, having the sequence 5'-GTTGGA GTCA CAGAGGCTAA GG-3', designated SEQ ID NO:23, to produce a polymerase chain reaction product from mouse spleen cDNA, generated by reverse transcription using standard techniques. The resulting PCR amplification product was a fragment of about 823 nucleotides, denoted herein as $nmCD23_{823}$. To identify a cDNA clone encoding a canine CD23 protein, $nmCD23_{823}$ was used as a probe as follows. Nucleic acid molecule $mCD23_{823}$ was labeled with $^{32}P$ and used as a probe to screen a *C. familiaris* mitogen-activated PBMC cDNA library that was constructed in the Uni-ZAP®XR vector (available from Stratagene Cloning Systems, La Jolla, Calif.), using Stratagene's ZAP-cDNA®Synthesis Kit and the manufacturer's protocol. The mRNA was isolated from *C. familiaris* peripheral blood mononuclear cells about 4 hours after they were activated by a polyclonal activating agent in culture. Hybridization was carried out in 6×SSC, 5×Denhardt's solution, (for recipe see Sambrook, et al., ibid), 0.5% sodium dodecyl sulfate, (SDS), 100 μg/ml of single stranded DNA (ssDNA) at 55° C., for 18 hours. The filters were washed 3 times, for about 30 minutes each wash, at 55° C. in 6×SSC, 0.2% SDS, followed by a final wash of about 30 minutes at 55° C. in 0.2×SSC, 0.1% SDS. Positive clones were identified and further purified. Both strands of inserts in the cDNA clones were sequenced using vector flanking primers and gene-specific internal primers. Sequence analysis was performed using the GAP program of GCG (available from the University of Wisconsin) using the alignment settings of: gap weight set at 50, length weight set at 3, and average match set at 10 for nucleic acid sequence comparisons; and gap weight set at 12, length weight set at 4, and average match set at 2.912 for amino acid sequence comparisons.

A clone was isolated, referred to herein as $nCaCD23_{2851}$, the coding strand of which was shown to have a nucleic acid sequence denoted herein as SEQ ID NO:1. The complement of SEQ ID NO:1 is represented herein by SEQ ID NO:3. Translation of SEQ ID NO:1 suggests that nucleic acid molecule $nCaCD23_{285}$ encodes a full-length CD23 protein of about 292 amino acids, denoted herein as $PCaCD23_{292}$, the amino acid sequence of which is presented in SEQ ID NO:2 and SEQ ID NO:5, assuming an open reading frame having an initiation codon spanning from nucleotide 199 through nucleotide 201 of SEQ ID NO:1 and a stop codon spanning from nucleotide 1075 through nucleotide 1077 of SEQ ID NO:1. The coding region encoding $PCaCD23_{292}$ is presented herein as $nCaCD23_{876}$, which has the nucleotide sequence SEQ ID NO:4 (the coding strand) and SEQ ID NO:6 (the complementary strand); this coding region does not include the stop codon.

Comparison of nucleic acid sequence SEQ ID NO:1 with nucleic acid sequences reported in GenBank indicates that SEQ ID NO:1 shared the most similarity with a human CD23 gene (Genbank Accession number XO4772). Comparison of SEQ ID NO:4, the coding region of SEQ ID NO:1, was 89.3% identical with the human CD23 coding region. Comparison of amino acid sequence SEQ ID NO:2 with amino acid sequences reported in Genbank indicates that SEQ ID NO:2 shared the most similarity, i.e., about 64% identity, with a human CD23 protein (P06734). Sequence analysis was performed using the GCG GAP program as described above.

What is claimed is:

1. An isolated nucleic acid molecule selected from the group consisting of:
   (a) an isolated nucleic acid molecule comprising a nucleic acid sequence selected from the group consisting of SEQ ID NO:1, SEQ ID NO:4, SEQ ID NO:7, SEQ ID NO:10, SEQ ID NO:13, SEQ ID NO:16, SEQ ID NO:19 and SEQ ID NO:24; and
   (b) an isolated nucleic acid molecule complementary to the isolated nucleic acid molecule of (a), wherein said complementary nucleic acid molecule comprises a nucleic acid sequence selected from the group consisting of SEQ ID NO:3, SEQ ID NO:6, SEQ ID NO:9, SEQ ID NO:12, SEQ ID NO:15, SEQ ID NO:18, SEQ ID NO:21 and SEQ ID NO:26.

2. The isolated nucleic acid molecule of claim 1, wherein said nucleic acid molecule comprises a nucleic acid sequence selected from the group consisting of SEQ ID NO:1, SEQ ID NO:4, SEQ ID NO:7, SEQ ID NO:10, SEQ ID NO:13, SEQ ID NO:16, SEQ ID NO:19 and SEQ ID NO:24.

3. The isolated nucleic acid molecule of claim 1, wherein said nucleic acid molecule comprises a nucleic acid sequence selected from the group consisting of SEQ ID NO:3, SEQ ID NO:6, SEQ ID NO:9, SEQ ID NO:12, SEQ ID NO:15, SEQ ID NO:18, SEQ ID NO:21 and SEQ ID NO:26.

4. A recombinant molecule comprising a nucleic acid molecule as set forth in claim 1 operatively linked to a transcription control sequence.

5. A recombinant virus comprising a nucleic acid molecule as set forth in claim 1.

6. A recombinant cell comprising a nucleic acid molecule as set forth in claim 1.

7. A method to produce a CD23 protein comprising culturing a cell transformed with a nucleic acid molecule encoding a protein comprising an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20 and SEQ ID NO:25 and recovering the express CD23 protein.

8. An isolated nucleic acid molecule selected from the group consisting of:
   (a) an isolated nucleic acid molecule encoding a protein comprising an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20 and SEQ ID NO:25, and
   (b) an isolated nucleic acid molecule complementary to the isolated nucleic acid molecule of (a).

9. A recombinant molecule comprising a nucleic acid molecule as set forth in claim 8 operatively linked to a transcription control sequence.

10. A recombinant virus comprising a nucleic acid molecule as set forth in claim 8.

11. A recombinant cell comprising a nucleic acid molecule as set forth in claim 8.

* * * * *

SEQUENCE LISTING

<160> NUMBER OF SEQ ID NOS: 26

<210> SEQ ID NO 1
<211> LENGTH: 2851
<212> TYPE: DNA
<213> ORGANISM: Canis familiaris
<220> FEATURE:
<221> NAME/KEY: CDS
<222> LOCATION: (199)..(1077)

<400> SEQUENCE: 1
gttaagcggc tcaccacggc ctgcggcccc gccagcctct cgggtcagcc c cttccgggc      60 cggcgacaca ctcacaactc atgtgagtgc gtggtaggcg tgatgtaacc c agatcccgg     120

-continued

```
ccagagctat acctgttgag cggactgctt tgtcaggtgg tgagcagccc g tcactgggg        180 aatccaagca cagttgac atg gag gaa cat tca tac tca gac cca gca gag           231
                    Met Glu Glu His Ser Tyr Ser Asp Pro Ala Glu
                     1               5                  10 ttc cca aag ttt tcc aga aga cgg cgg tgc t gt agg ccc ggg gtg cag          279
Phe Pro Lys Phe Ser Arg Arg Arg Arg Cys C ys Arg Pro Gly Val Gln
            15                  20                  25 ctg gcg ctg ctg ggg ctg gtg act gtc atg c tg tgg gcc ggg ctg ctg          327
Leu Ala Leu Leu Gly Leu Val Thr Val Met L eu Trp Ala Gly Leu Leu
        30                  35                  40 acc ctg ctc ctc ttc tgg cac agg gac act g ta cag aat ctg aaa cag          375
Thr Leu Leu Leu Phe Trp His Arg Asp Thr V al Gln Asn Leu Lys Gln
    45                  50                  55 ctg gag gtc gcc gcc gcc cag aac gtc tct c gg gtt tcc aag gac ttg          423
Leu Glu Val Ala Ala Ala Gln Asn Val Ser A rg Val Ser Lys Asp Leu
60                  65                  70                  75 gaa aga cac aac ggt gac cag atg gcc cag a aa tcc cag gct gcc cag          471
Glu Arg His Asn Gly Asp Gln Met Ala Gln L ys Ser Gln Ala Ala Gln
                80                  85                  90 gtg tca cag gac atg aag gaa atc caa gct g aa cag aag aga atg aaa          519
Val Ser Gln Asp Met Lys Glu Ile Gln Ala G lu Gln Lys Arg Met Lys
            95                  100                 105 gct cag gac tct gag ctc tcc cag aac ctg g at gca ctt cgt tcg gac          567
Ala Gln Asp Ser Glu Leu Ser Gln Asn Leu A sp Ala Leu Arg Ser Asp
        110                 115                 120 ctg aac aac ctc aag tcc cag agc ttg aac g ag aga agc aca gcc ttg          615
Leu Asn Asn Leu Lys Ser Gln Ser Leu Asn G lu Arg Ser Thr Ala Leu
    125                 130                 135 cat tca ctg gag aga ctc cag gag gag gtg g ag aag ctg tgg atg gag          663
His Ser Leu Glu Arg Leu Gln Glu Glu Val G lu Lys Leu Trp Met Glu
140                 145                 150                 155 cta cac gtg tcc aac ggc tcc gag tgt aac a cg tgc cct gag aag tgg          711
Leu His Val Ser Asn Gly Ser Glu Cys Asn T hr Cys Pro Glu Lys Trp
                160                 165                 170 ctc aac ttc cag agg aag tgc tac tac ttc g gc gag gag ccc aag aag          759
Leu Asn Phe Gln Arg Lys Cys Tyr Tyr Phe G ly Glu Glu Pro Lys Lys
            175                 180                 185 tgg atc cag gcc cgg ttt gcc tgc agc aag c tg caa ggg cgg ctg gcc          807
Trp Ile Gln Ala Arg Phe Ala Cys Ser Lys L eu Gln Gly Arg Leu Ala
        190                 195                 200 agc atc cac agc caa gag gag cag gac ttc c tg gcc agg tat gcc aac          855
Ser Ile His Ser Gln Glu Glu Gln Asp Phe L eu Ala Arg Tyr Ala Asn
    205                 210                 215 aag aag ggc acc tgg att ggc ctc cgg gac c tg gac aga gag ggg gag          903
Lys Lys Gly Thr Trp Ile Gly Leu Arg Asp L eu Asp Arg Glu Gly Glu
220                 225                 230                 235 ttt atc tgg atg gac gag aac ccc ctg aac t at agc aac tgg cgg ccc          951
Phe Ile Trp Met Asp Glu Asn Pro Leu Asn T yr Ser Asn Trp Arg Pro
                240                 245                 250 ggg gag ccc aac aac ggg ggc cag ggc gag g ac tgc gtg atg atg cag          999
Gly Glu Pro Asn Asn Gly Gly Gln Gly Glu A sp Cys Val Met Met Gln
            255                 260                 265 ggc tcg ggg cag tgg aat gac gcc ttc tgc g gc agc tcg ctg gac ggc          1047
Gly Ser Gly Gln Trp Asn Asp Ala Phe Cys G ly Ser Ser Leu Asp Gly
        270                 275                 280 tgg gtg tgt gac cgg ctg gcc acg tgc tga c tgcccaccg gccgcctcgg            1097
Trp Val Cys Asp Arg Leu Ala Thr Cys
        285                 290 caccccgggg ttcgctggga tgtgctccga gacacacacc ccgacggccc c ctgcccgcc        1157
```

-continued

```
ctgccaggtg caccgcctcc gtcgctcccc aggtacagcc aggccccect g cagggctct      1217
gaggaccctc caccatttgg ggttaaggtc ccggcaacac ttccttgcgc c caaatggga      1277
gaagggctgt tgacacaccc cagctcctgc caatccccag agggcccgtc c cttgctcct     1337
cagcccagcc cggctggctg tcaccgcgtc cctgccttca agcgctcgga g tacccacct     1397
cagaactttc cggggagcag tggtggatgc ctcagactcc tgggtggggc c cacccacct     1457
tctgctggag tcaggagtca accacacccc caccccagcc ccggcctccc t agatgcagc     1517
ctcgggtcc taccccccag ccaggctccc cagccagccc atgtcgataa a atggggcga      1577
ggatggcccc ctctcagggg cctcgctggc tctggtctcc agatatggga g ctgggagct     1637
ccagaacctg gtgcctgagg ccacctctga gtttccagaa caactgaagc g gtatttgta    1697
cttcgccacc tttatccagc gacccccccc ccccgccac tttatttcaa g aagcattta     1757
ctagacaggg ctggagagga agactctggg gtctgataca gcagagaaca c ccttagacc    1817
ctcaagaata tcgcaggcca ccccaattcc tgcaaaagc agaaggaacc a gagatgtgc     1877
tcgtgatact caggcccctt ggagggaat ccacgaggag gggcccacac t ggaccgcgc     1937
gggacccggg agtcacgggc caggccaggg ggctggggag ggcgccgcat t ggcacctag   1997
gagtcctgcg gccaggagg ggcggggca gggctagtcc taggtcccct g ttgtctacc      2057
ccctgctcac cctgtttgtg cctcctccag tccccccacc ctgaactctg g gccagagta    2117
gaactgtctc cctgagctct ctaaagggga ctcccgccc cgccctgcca c ccagaccac     2177
attggggtca caagcagcac ctgtttccct ccctgccccc tctgaatctt c agggaaagc    2237
cttgtgcaca atctgcccac ttcccaccgc ctccggcaaa ccgctttgga g tagccccca   2297
tcccagcctg cctcagtctc cttcttcacc gccccacacc ttccagaatt t ccttctgc    2357
ctctgagggg aaaacaaaaa caaacccaga gtctcatagg gagctttgca a tggcagatc    2417
ccctgcgact tgccttgtct ccccagcttc acctccgctc tctcctccgc c agccccagc   2477
ctcctctctg gcccttccac atggaggctt gctcctgccc cagggccttt g cacatgtcc   2537
ctcccccac tcgctcctca gtgagggcta tcctgggctc ctccccctc t cgtttaaaa     2597
ctgcaccccg actccagatc cctttttatgc tgccctactt gatcgccttg g actcttccc   2657
cttctgagaa aatgtatcat ccaccgctct gtgtgttccg tcccctggg g cttgaatgt     2717
gagcctcgag gagggagctt ttgttttgct ctgggacgcc agcgcctgac a catagtagg   2777
tgttcaataa agagctttc cgaaaaatga aaaaaaaaa aaaaaaaaa a aaaaaaaa        2837
aaaaaaaaaa aaaa                                                         2851
```

<210> SEQ ID NO 2
<211> LENGTH: 292
<212> TYPE: PRT
<213> ORGANISM: Canis familiaris

<400> SEQUENCE: 2

```
Met Glu Glu His Ser Tyr Ser Asp Pro Ala Glu Phe Pro Lys Phe Ser
 1               5                  10                  15

Arg Arg Arg Arg Cys Cys Arg Pro Gly Val Gln Leu Ala Leu Leu Gly
                20                  25                  30

Leu Val Thr Val Met Leu Trp Ala Gly Leu Thr Leu Leu Leu Phe
            35                  40                  45

Trp His Arg Asp Thr Val Gln Asn Leu Lys Gln Leu Glu Val Ala Ala
        50                  55                  60
```

Ala Gln Asn Val Ser Arg Val Ser Lys Asp Leu Glu Arg His Asn Gly
 65                  70                  75                  80

Asp Gln Met Ala Gln Lys Ser Gln Ala Ala Gln Val Ser Gln Asp Met
                 85                  90                  95

Lys Glu Ile Gln Ala Glu Gln Lys Arg Met Lys Ala Gln Asp Ser Glu
            100                 105                 110

Leu Ser Gln Asn Leu Asp Ala Leu Arg Ser Asp Leu Asn Asn Leu Lys
        115                 120                 125

Ser Gln Ser Leu Asn Glu Arg Ser Thr Ala Leu His Ser Leu Glu Arg
130                 135                 140

Leu Gln Glu Glu Val Glu Lys Leu Trp Met Glu Leu His Val Ser Asn
145                 150                 155                 160

Gly Ser Glu Cys Asn Thr Cys Pro Glu Lys Trp Leu Asn Phe Gln Arg
                165                 170                 175

Lys Cys Tyr Tyr Phe Gly Glu Glu Pro Lys Lys Trp Ile Gln Ala Arg
            180                 185                 190

Phe Ala Cys Ser Lys Leu Gln Gly Arg Leu Ala Ser Ile His Ser Gln
        195                 200                 205

Glu Glu Gln Asp Phe Leu Ala Arg Tyr Ala Asn Lys Lys Gly Thr Trp
210                 215                 220

Ile Gly Leu Arg Asp Leu Asp Arg Glu Gly Glu Phe Ile Trp Met Asp
225                 230                 235                 240

Glu Asn Pro Leu Asn Tyr Ser Asn Trp Arg Pro Gly Glu Pro Asn Asn
                245                 250                 255

Gly Gly Gln Gly Glu Asp Cys Val Met Met Gln Gly Ser Gly Gln Trp
            260                 265                 270

Asn Asp Ala Phe Cys Gly Ser Ser Leu Asp Gly Trp Val Cys Asp Arg
        275                 280                 285

Leu Ala Thr Cys
    290

<210> SEQ ID NO 3
<211> LENGTH: 2851
<212> TYPE: DNA
<213> ORGANISM: Canis familiaris

<400> SEQUENCE: 3
tttttttttt tttttttttt tttttttttt tttttttttt tttttcattt ttcggaaaag      60
ctctttattg aacacctact atgtgtcagg cgctggcgtc ccagagcaaa acaaaagctc     120
cctcctcgag gctcacattc aagccccagg gggacggaac acacagagcg gtggatgata     180
cattttctca gaaggggaag agtccaaggc gatcaagtag gcagcataaa agggatctg     240 gagtcggggt gcagttttaa acgagagggg ggaggagccc aggatagccc tcactgagga     300
gcgagtgggg gagggacat gtgcaaaggc cctggggcag gagcaagcct ccatgtggaa     360
gggccagaga ggaggctggg gctggcggag gagagagcgg aggtgaagct gggagacaa     420 ggcaagtcgc agggggatctg ccattgcaaa gctccctatg agactctggg ttgttttttg     480 ttttccccctc agaggcagaa ggaaaattct ggaaggtgtg gggcggtgaa gaaggagact     540
gaggcaggct gggatggggg ctactccaaa gcggtttgcc ggaggcggtg ggaagtgggc     600
agattgtgca caaggctttc cctgaagatt cagaggggggc agggagggaa acaggtgctg     660
cttgtgaccc caatgtggtc tgggtggcag ggcggggccg ggagtcccct ttagagagct     720
cagggagaca gttctactct ggcccagagt tcagggtggg gggactggag gaggcacaaa     780

-continued

```
cagggtgagc aggggggtaga caacagggga cctaggacta gccctgcccc c gccccctccc    840 tggccgcagg actcctaggt gccaatgcgg cgccctcccc agcccctgg c ctggcccgt      900 gactcccggg tcccgcgcgg tccagtgtgg cccctcctc gtggattccc c tccaagggg     960 cctgagtatc acgagcacat ctctggttcc ttctgctttt gccaggaatt g gggtggcct    1020 gcgatattct tgagggtcta aggtgttct ctgctgtatc agaccccaga g tcttcctct    1080 ccagccctgt ctagtaaatg cttcttgaaa taaagtggcg gggggggggg g gtcgctgga    1140 taaaggtggc gaagtacaaa taccgcttca gttgttctgg aaactcagag g tggcctcag    1200 gcaccaggtt ctggagctcc cagctcccat atctggagac cagagccagc g aggcccctg    1260 agaggggggcc atcctcgccc cattttatcg acatgggctg ctggggagc c tggctgggg    1320 ggtaggaccc cgaggctgca tctagggagg ccggggctgg ggtggggtg t ggttgactc    1380 ctgactccag cagaaggtgg gtgggcccca cccaggagtc tgaggcatcc a ccactgctc    1440 cccggaaagt tctgaggtgg gtactccgag cgcttgaagg cagggacgcg g tgacagcca    1500 gccgggctgg gctgaggagc aagggacggg ccctctgggg attggcagga g ctgggtgt    1560 gtcaacagcc cttctcccat ttgggcgcaa ggaagtgttg ccgggacctt a accccaaat    1620 ggtggagggt cctcagagcc ctgcaggggg gcctggctgt acctggggag c gacggaggc    1680 ggtgcacctg gcagggcggg caggggggccg tcggggtgtg tgtctcggag c acatcccag    1740 cgaaccccgg ggtgccgagg cggccggtgg gcagtcagca cgtggccagc c ggtcacaca    1800 cccagccgtc cagcgagctg ccgcagaagg cgtcattcca ctgccccgag c cctgcatca    1860 tcacgcagtc ctcgccctgg cccccgttgt tgggctcccc gggccgccag t tgctatagt    1920 tcaggggggtt ctcgtccatc cagataaact ccccctctct gtccaggtcc c ggaggccaa    1980 tccaggtgcc cttcttgttg gcatacctgg ccaggaagtc ctgctcctct t ggctgtgga    2040 tgctggccag ccgcccttgc agcttgctgc aggcaaaccg gcctggatc c acttcttgg    2100 gctcctcgcc gaagtagtag cacttcctct ggaagttgag ccacttctca g gcacgtgt    2160 tacactcgga gccgttggac acgtgtagct ccatccacag cttctccacc t cctcctgga    2220 gtctctccag tgaatgcaag gctgtgcttc tctcgttcaa gctctgggac t tgaggttgt    2280 tcaggtccga acgaagtgca tccaggttct gggagagctc agagtcctga g cttcattc    2340 tcttctgttc agcttggatt tccttcatgt cctgtgacac ctgggcagcc t gggatttct    2400 gggccatctg gtcaccgttg tgtctttcca agtccttgga aacccgagag a cgttctggg    2460 cggcggcgac ctccagctgt ttcagattct gtacagtgtc cctgtgccag a agaggagca    2520 gggtcagcag cccggcccac agcatgacag tcaccagccc cagcagcgcc a gctgcaccc    2580 cgggcctaca gcaccgccgt cttctggaaa actttgggaa ctctgctggg t ctgagtatg    2640 aatgttcctc catgtcaact gtgcttggat tccccagtga cgggctgctc a ccacctgac    2700 aaagcagtcc gctcaacagg tatagctctg gccgggatct gggttacatc a cgcctacca    2760 cgcactcaca tgagttgtga gtgtgtcgcc ggcccggaag gggctgaccc g agaggctgg    2820 cggggccgca ggccgtggtg agccgcttaa c                                    2851
```

<210> SEQ ID NO 4
<211> LENGTH: 876
<212> TYPE: DNA
<213> ORGANISM: Canis familiaris
<220> FEATURE:
<221> NAME/KEY: CDS
<222> LOCATION: (1)..(876)

```
<400> SEQUENCE: 4 atg gag gaa cat tca tac tca gac cca gca g ag ttc cca aag ttt tcc        48
Met Glu Glu His Ser Tyr Ser Asp Pro Ala G lu Phe Pro Lys Phe Ser
  1               5                  10                 15 aga aga cgg cgg tgc tgt agg ccc ggg gtg c ag ctg gcg ctg ctg ggg        96
Arg Arg Arg Arg Cys Cys Arg Pro Gly Val G ln Leu Ala Leu Leu Gly
                 20                  25                 30 ctg gtg act gtc atg ctg tgg gcc ggg ctg c tg acc ctg ctc ctc ttc       144
Leu Val Thr Val Met Leu Trp Ala Gly Leu L eu Thr Leu Leu Leu Phe
             35                  40                 45 tgg cac agg gac act gta cag aat ctg aaa c ag ctg gag gtc gcc gcc       192
Trp His Arg Asp Thr Val Gln Asn Leu Lys G ln Leu Glu Val Ala Ala
         50                  55                 60 gcc cag aac gtc tct cgg gtt tcc aag gac t tg gaa aga cac aac ggt       240
Ala Gln Asn Val Ser Arg Val Ser Lys Asp L eu Glu Arg His Asn Gly
     65                  70                  75                 80 gac cag atg gcc cag aaa tcc cag gct gcc c ag gtg tca cag gac atg       288
Asp Gln Met Ala Gln Lys Ser Gln Ala Ala G ln Val Ser Gln Asp Met
                 85                  90                 95 aag gaa atc caa gct gaa cag aag aga atg a aa gct cag gac tct gag       336
Lys Glu Ile Gln Ala Glu Gln Lys Arg Met L ys Ala Gln Asp Ser Glu
                100                 105                110 ctc tcc cag aac ctg gat gca ctt cgt tcg g ac ctg aac aac ctc aag       384
Leu Ser Gln Asn Leu Asp Ala Leu Arg Ser A sp Leu Asn Asn Leu Lys
            115                 120                 125 tcc cag agc ttg aac gag aga agc aca gcc t tg cat tca ctg gag aga       432
Ser Gln Ser Leu Asn Glu Arg Ser Thr Ala L eu His Ser Leu Glu Arg
        130                 135                 140 ctc cag gag gag gtg gag aag ctg tgg atg g ag cta cac gtg tcc aac       480
Leu Gln Glu Glu Val Glu Lys Leu Trp Met G lu Leu His Val Ser Asn
145                 150                 155                 160 ggc tcc gag tgt aac acg tgc cct gag aag t gg ctc aac ttc cag agg       528
Gly Ser Glu Cys Asn Thr Cys Pro Glu Lys T rp Leu Asn Phe Gln Arg
                165                 170                 175 aag tgc tac tac ttc ggc gag gag ccc aag a ag tgg atc cag gcc cgg       576
Lys Cys Tyr Tyr Phe Gly Glu Glu Pro Lys L ys Trp Ile Gln Ala Arg
            180                 185                 190 ttt gcc tgc agc aag ctg caa ggg cgg ctg g cc agc atc cac agc caa       624
Phe Ala Cys Ser Lys Leu Gln Gly Arg Leu A la Ser Ile His Ser Gln
        195                 200                 205 gag gag cag gac ttc ctg gcc agg tat gcc a ac aag aag ggc acc tgg       672
Glu Glu Gln Asp Phe Leu Ala Arg Tyr Ala A sn Lys Lys Gly Thr Trp
    210                 215                 220 att ggc ctc cgg gac ctg gac aga gag ggg g ag ttt atc tgg atg gac       720
Ile Gly Leu Arg Asp Leu Asp Arg Glu Gly G lu Phe Ile Trp Met Asp
225                 230                 235                 240 gag aac ccc ctg aac tat agc aac tgg cgg c cc ggg gag ccc aac aac       768
Glu Asn Pro Leu Asn Tyr Ser Asn Trp Arg P ro Gly Glu Pro Asn Asn
                245                 250                 255 ggg ggc cag ggc gag gac tgc gtg atg atg c ag ggc tcg ggg cag tgg       816
Gly Gly Gln Gly Glu Asp Cys Val Met Met G ln Gly Ser Gly Gln Trp
            260                 265                 270 aat gac gcc ttc tgc ggc agc tcg ctg gac g gc tgg gtg tgt gac cgg       864
Asn Asp Ala Phe Cys Gly Ser Ser Leu Asp G ly Trp Val Cys Asp Arg
        275                 280                 285 ctg gcc acg tgc                                                        876
Leu Ala Thr Cys
    290
```

```
<210> SEQ ID NO 5
<211> LENGTH: 292
<212> TYPE: PRT
<213> ORGANISM: Canis familiaris

<400> SEQUENCE: 5
```

| Met | Glu | Glu | His | Ser | Tyr | Ser | Asp | Pro | Ala | Glu | Phe | Pro | Lys | Phe | Ser |
|---|---|---|---|---|---|---|---|---|---|---|---|---|---|---|---|
| 1 | | | | 5 | | | | | 10 | | | | | 15 | |

| Arg | Arg | Arg | Arg | Cys | Cys | Arg | Pro | Gly | Val | Gln | Leu | Ala | Leu | Leu | Gly |
|---|---|---|---|---|---|---|---|---|---|---|---|---|---|---|---|
| | | | 20 | | | | | 25 | | | | | 30 | | |

| Leu | Val | Thr | Val | Met | Leu | Trp | Ala | Gly | Leu | Leu | Thr | Leu | Leu | Leu | Phe |
|---|---|---|---|---|---|---|---|---|---|---|---|---|---|---|---|
| | | 35 | | | | | 40 | | | | | 45 | | | |

| Trp | His | Arg | Asp | Thr | Val | Gln | Asn | Leu | Lys | Gln | Leu | Glu | Val | Ala | Ala |
|---|---|---|---|---|---|---|---|---|---|---|---|---|---|---|---|
| 50 | | | | | 55 | | | | | 60 | | | | | |

| Ala | Gln | Asn | Val | Ser | Arg | Val | Ser | Lys | Asp | Leu | Glu | Arg | His | Asn | Gly |
|---|---|---|---|---|---|---|---|---|---|---|---|---|---|---|---|
| 65 | | | | 70 | | | | | 75 | | | | | 80 | |

| Asp | Gln | Met | Ala | Gln | Lys | Ser | Gln | Ala | Ala | Gln | Val | Ser | Gln | Asp | Met |
|---|---|---|---|---|---|---|---|---|---|---|---|---|---|---|---|
| | | | | 85 | | | | | 90 | | | | | 95 | |

| Lys | Glu | Ile | Gln | Ala | Glu | Gln | Lys | Arg | Met | Lys | Ala | Gln | Asp | Ser | Glu |
|---|---|---|---|---|---|---|---|---|---|---|---|---|---|---|---|
| | | | 100 | | | | | 105 | | | | | 110 | | |

| Leu | Ser | Gln | Asn | Leu | Asp | Ala | Leu | Arg | Ser | Asp | Leu | Asn | Asn | Leu | Lys |
|---|---|---|---|---|---|---|---|---|---|---|---|---|---|---|---|
| | | 115 | | | | | 120 | | | | | 125 | | | |

| Ser | Gln | Ser | Leu | Asn | Glu | Arg | Ser | Thr | Ala | Leu | His | Ser | Leu | Glu | Arg |
|---|---|---|---|---|---|---|---|---|---|---|---|---|---|---|---|
| | 130 | | | | | 135 | | | | | 140 | | | | |

| Leu | Gln | Glu | Glu | Val | Glu | Lys | Leu | Trp | Met | Glu | Leu | His | Val | Ser | Asn |
|---|---|---|---|---|---|---|---|---|---|---|---|---|---|---|---|
| 145 | | | | | 150 | | | | | 155 | | | | | 160 |

| Gly | Ser | Glu | Cys | Asn | Thr | Cys | Pro | Glu | Lys | Trp | Leu | Asn | Phe | Gln | Arg |
|---|---|---|---|---|---|---|---|---|---|---|---|---|---|---|---|
| | | | | 165 | | | | | 170 | | | | | 175 | |

| Lys | Cys | Tyr | Tyr | Phe | Gly | Glu | Glu | Pro | Lys | Lys | Trp | Ile | Gln | Ala | Arg |
|---|---|---|---|---|---|---|---|---|---|---|---|---|---|---|---|
| | | | 180 | | | | | 185 | | | | | 190 | | |

| Phe | Ala | Cys | Ser | Lys | Leu | Gln | Gly | Arg | Leu | Ala | Ser | Ile | His | Ser | Gln |
|---|---|---|---|---|---|---|---|---|---|---|---|---|---|---|---|
| | | 195 | | | | | 200 | | | | | 205 | | | |

| Glu | Glu | Gln | Asp | Phe | Leu | Ala | Arg | Tyr | Ala | Asn | Lys | Lys | Gly | Thr | Trp |
|---|---|---|---|---|---|---|---|---|---|---|---|---|---|---|---|
| | 210 | | | | | 215 | | | | | 220 | | | | |

| Ile | Gly | Leu | Arg | Asp | Leu | Asp | Arg | Glu | Gly | Glu | Phe | Ile | Trp | Met | Asp |
|---|---|---|---|---|---|---|---|---|---|---|---|---|---|---|---|
| 225 | | | | | 230 | | | | | 235 | | | | | 240 |

| Glu | Asn | Pro | Leu | Asn | Tyr | Ser | Asn | Trp | Arg | Pro | Gly | Glu | Pro | Asn | Asn |
|---|---|---|---|---|---|---|---|---|---|---|---|---|---|---|---|
| | | | | 245 | | | | | 250 | | | | | 255 | |

| Gly | Gly | Gln | Gly | Glu | Asp | Cys | Val | Met | Met | Gln | Gly | Ser | Gly | Gln | Trp |
|---|---|---|---|---|---|---|---|---|---|---|---|---|---|---|---|
| | | | 260 | | | | | 265 | | | | | 270 | | |

| Asn | Asp | Ala | Phe | Cys | Gly | Ser | Ser | Leu | Asp | Gly | Trp | Val | Cys | Asp | Arg |
|---|---|---|---|---|---|---|---|---|---|---|---|---|---|---|---|
| | | 275 | | | | | 280 | | | | | 285 | | | |

| Leu | Ala | Thr | Cys |
|---|---|---|---|
| | 290 | | |

```
<210> SEQ ID NO 6
<211> LENGTH: 876
<212> TYPE: DNA
<213> ORGANISM: Canis familiaris

<400> SEQUENCE: 6
gcacgtggcc agccggtcac acacccagcc gtccagcgag ctgccgcaga a ggcgtcatt      60 ccactgcccc gagccctgca tcatcacgca gtcctcgccc tggccccgt t gttgggctc     120 cccgggccgc cagttgctat agttcagggg gttctcgtcc atccagataa a ctccccctc    180 tctgtccagg tcccggaggc caatccaggt gcccttcttg ttggcatacc t ggccaggaa    240
```

```
gtcctgctcc tcttggctgt ggatgctggc cagccgccct tgcagcttgc t gcaggcaaa      300 ccgggcctgg atccacttct tgggctcctc gccgaagtag tagcacttcc t ctggaagtt      360 gagccacttc tcagggcacg tgttacactc ggagccgttg acacgtgta g ctccatcca      420 cagcttctcc acctcctcct ggagtctctc cagtgaatgc aaggctgtgc t tctctcgtt      480 caagctctgg gacttgaggt tgttcaggtc cgaacgaagt gcatccaggt t ctgggagag      540 ctcagagtcc tgagctttca ttctcttctg ttcagcttgg atttccttca t gtcctgtga      600 cacctgggca gcctgggatt tctgggccat ctggtcaccg ttgtgtcttt c caagtcctt      660 ggaaacccga gagacgttct gggcggcggc gacctccagc tgtttcagat t ctgtacagt      720 gtccctgtgc cagaagagga gcagggtcag cagcccggcc acagcatga c agtcaccag      780 ccccagcagc gccagctgca ccccgggcct acagcaccgc cgtcttctgg a aactttgg      840 gaactctgct gggtctgagt atgaatgttc ctccat                                876

<210> SEQ ID NO 7
<211> LENGTH: 384
<212> TYPE: DNA
<213> ORGANISM: Canis familiaris
<220> FEATURE:
<221> NAME/KEY: CDS
<222> LOCATION: (1)..(384)

<400> SEQUENCE: 7 aac acg tgc cct gag aag tgg ctc aac ttc c ag agg aag tgc tac tac            48
Asn Thr Cys Pro Glu Lys Trp Leu Asn Phe G ln Arg Lys Cys Tyr Tyr
  1               5                  10                  15 ttc ggc gag gag ccc aag aag tgg atc cag g cc cgg ttt gcc tgc agc            96
Phe Gly Glu Glu Pro Lys Lys Trp Ile Gln A la Arg Phe Ala Cys Ser
             20                  25                  30 aag ctg caa ggg cgg ctg gcc agc atc cac a gc caa gag gag cag gac           144
Lys Leu Gln Gly Arg Leu Ala Ser Ile His S er Gln Glu Glu Gln Asp
         35                  40                  45 ttc ctg gcc agg tat gcc aac aag aag ggc a cc tgg att ggc ctc cgg           192
Phe Leu Ala Arg Tyr Ala Asn Lys Lys Gly T hr Trp Ile Gly Leu Arg
     50                  55                  60 gac ctg gac aga gag ggg gag ttt atc tgg a tg gac gag aac ccc ctg           240
Asp Leu Asp Arg Glu Gly Glu Phe Ile Trp M et Asp Glu Asn Pro Leu
 65                  70                  75                  80 aac tat agc aac tgg cgg ccc ggg gag ccc a ac aac ggg ggc cag ggc           288
Asn Tyr Ser Asn Trp Arg Pro Gly Glu Pro A sn Asn Gly Gly Gln Gly
                 85                  90                  95 gag gac tgc gtg atg atg cag ggc tcg ggg c ag tgg aat gac gcc ttc           336
Glu Asp Cys Val Met Met Gln Gly Ser Gly G ln Trp Asn Asp Ala Phe
            100                 105                 110 tgc ggc agc tcg ctg gac ggc tgg gtg tgt g ac cgg ctg gcc acg tgc           384
Cys Gly Ser Ser Leu Asp Gly Trp Val Cys A sp Arg Leu Ala Thr Cys
        115                 120                 125

<210> SEQ ID NO 8
<211> LENGTH: 128
<212> TYPE: PRT
<213> ORGANISM: Canis familiaris

<400> SEQUENCE: 8

Asn Thr Cys Pro Glu Lys Trp Leu Asn Phe G ln Arg Lys Cys Tyr Tyr
  1               5                  10                  15

Phe Gly Glu Glu Pro Lys Lys Trp Ile Gln A la Arg Phe Ala Cys Ser
             20                  25                  30
```

```
Lys Leu Gln Gly Arg Leu Ala Ser Ile His S er Gln Glu Glu Gln Asp
         35                  40                  45

Phe Leu Ala Arg Tyr Ala Asn Lys Lys Gly T hr Trp Ile Gly Leu Arg
     50                  55                  60

Asp Leu Asp Arg Glu Gly Glu Phe Ile Trp M et Asp Glu Asn Pro Leu
 65                  70                  75                  80

Asn Tyr Ser Asn Trp Arg Pro Gly Glu Pro A sn Asn Gly Gly Gln Gly
                 85                  90                  95

Glu Asp Cys Val Met Met Gln Gly Ser Gly G ln Trp Asn Asp Ala Phe
            100                 105                 110

Cys Gly Ser Ser Leu Asp Gly Trp Val Cys A sp Arg Leu Ala Thr Cys
            115                 120                 125

<210> SEQ ID NO 9
<211> LENGTH: 384
<212> TYPE: DNA
<213> ORGANISM: Canis familiaris

<400> SEQUENCE: 9
gcacgtggcc agccggtcac acacccagcc gtccagcgag ctgccgcaga a ggcgtcatt      60 ccactgcccc gagccctgca tcatcacgca gtcctcgccc tggcccccgt t gttgggctc    120 cccgggccgc cagttgctat agttcagggg gttctcgtcc atccagataa a ctccccctc    180 tctgtccagg tcccggaggc caatccaggt gcccttcttg ttggcatacc t ggccaggaa    240 gtcctgctcc tcttggctgt ggatgctggc cagccgccct gcagcttgc t gcaggcaaa    300 ccgggcctgg atccacttct tgggctcctc gccgaagtag tagcacttcc t ctggaagtt    360 gagccacttc tcagggcacg tgtt                                            384

<210> SEQ ID NO 10
<211> LENGTH: 417
<212> TYPE: DNA
<213> ORGANISM: Canis familiaris
<220> FEATURE:
<221> NAME/KEY: CDS
<222> LOCATION: (1)..(417)

<400> SEQUENCE: 10 atg gag cta cac gtg tcc aac ggc tcc gag t gt aac acg tgc cct gag      48
Met Glu Leu His Val Ser Asn Gly Ser Glu C ys Asn Thr Cys Pro Glu
 1               5                  10                  15 aag tgg ctc aac ttc cag agg aag tgc tac t ac ttc ggc gag gag ccc      96
Lys Trp Leu Asn Phe Gln Arg Lys Cys Tyr T yr Phe Gly Glu Glu Pro
             20                  25                  30 aag aag tgg atc cag gcc cgg ttt gcc tgc a gc aag ctg caa ggg cgg    144
Lys Lys Trp Ile Gln Ala Arg Phe Ala Cys S er Lys Leu Gln Gly Arg
         35                  40                  45 ctg gcc agc atc cac agc caa gag gag cag g ac ttc ctg gcc agg tat    192
Leu Ala Ser Ile His Ser Gln Glu Glu Gln A sp Phe Leu Ala Arg Tyr
     50                  55                  60 gcc aac aag aag ggc acc tgg att ggc ctc c gg gac ctg gac aga gag    240
Ala Asn Lys Lys Gly Thr Trp Ile Gly Leu A rg Asp Leu Asp Arg Glu
 65                  70                  75                  80 ggg gag ttt atc tgg atg gac gag aac ccc c tg aac tat agc aac tgg    288
Gly Glu Phe Ile Trp Met Asp Glu Asn Pro L eu Asn Tyr Ser Asn Trp
                 85                  90                  95 cgg ccc ggg gag ccc aac aac ggg ggc cag g gc gag gac tgc gtg atg    336
Arg Pro Gly Glu Pro Asn Asn Gly Gly Gln G ly Glu Asp Cys Val Met
            100                 105                 110
```

```
atg cag ggc tcg ggg cag tgg aat gac gcc t tc tgc ggc agc tcg ctg      384
Met Gln Gly Ser Gly Gln Trp Asn Asp Ala P he Cys Gly Ser Ser Leu
    115                 120                 125 gac ggc tgg gtg tgt gac cgg ctg gcc acg t gc                          417
Asp Gly Trp Val Cys Asp Arg Leu Ala Thr C ys
    130                 135
```

<210> SEQ ID NO 11
<211> LENGTH: 139
<212> TYPE: PRT
<213> ORGANISM: Canis familiaris

<400> SEQUENCE: 11

```
Met Glu Leu His Val Ser Asn Gly Ser Glu C ys Asn Thr Cys Pro Glu
  1               5                  10                  15

Lys Trp Leu Asn Phe Gln Arg Lys Cys Tyr T yr Phe Gly Glu Glu Pro
             20                  25                  30

Lys Lys Trp Ile Gln Ala Arg Phe Ala Cys S er Lys Leu Gln Gly Arg
         35                  40                  45

Leu Ala Ser Ile His Ser Gln Glu Glu Gln A sp Phe Leu Ala Arg Tyr
     50                  55                  60

Ala Asn Lys Lys Gly Thr Trp Ile Gly Leu A rg Asp Leu Asp Arg Glu
 65                  70                  75                  80

Gly Glu Phe Ile Trp Met Asp Glu Asn Pro L eu Asn Tyr Ser Asn Trp
                 85                  90                  95

Arg Pro Gly Glu Pro Asn Asn Gly Gly Gln G ly Glu Asp Cys Val Met
            100                 105                 110

Met Gln Gly Ser Gly Gln Trp Asn Asp Ala P he Cys Gly Ser Ser Leu
        115                 120                 125

Asp Gly Trp Val Cys Asp Arg Leu Ala Thr C ys
    130                 135
```

<210> SEQ ID NO 12
<211> LENGTH: 417
<212> TYPE: DNA
<213> ORGANISM: Canis familiaris

<400> SEQUENCE: 12

```
gcacgtggcc agccggtcac acacccagcc gtccagcgag ctgccgcaga a ggcgtcatt      60 ccactgcccc gagccctgca tcatcacgca gtcctcgccc tggcccccgt t gttgggctc     120 cccgggccgc cagttgctat agttcagggg gttctcgtcc atccagataa a ctcccccctc   180 tctgtccagg tcccggaggc caatccaggt gcccttcttg ttggcatacc t ggccaggaa    240 gtcctgctcc tcttggctgt ggatgctggc cagccgccct gcagcttgc t gcaggcaaa    300 ccgggcctgg atccacttct gggctcctc gccgaagtag tagcacttcc t ctggaagtt    360 gagccacttc tcagggcacg tgttacactc ggagccgttg acacgtgta g ctccat       417
```

<210> SEQ ID NO 13
<211> LENGTH: 423
<212> TYPE: DNA
<213> ORGANISM: Canis familiaris
<220> FEATURE:
<221> NAME/KEY: CDS
<222> LOCATION: (1)..(423)

<400> SEQUENCE: 13

```
ctg tgg atg gag cta cac gtg tcc aac ggc t cc gag tgt aac acg tgc      48
Leu Trp Met Glu Leu His Val Ser Asn Gly S er Glu Cys Asn Thr Cys
```

```
cct gag aag tgg ctc aac ttc cag agg aag t gc tac tac ttc ggc gag       96
Pro Glu Lys Trp Leu Asn Phe Gln Arg Lys C ys Tyr Tyr Phe Gly Glu
                 20                  25              30 gag ccc aag aag tgg atc cag gcc cgg ttt g cc tgc agc aag ctg caa      144
Glu Pro Lys Lys Trp Ile Gln Ala Arg Phe A la Cys Ser Lys Leu Gln
         35                  40              45 ggg cgg ctg gcc agc atc cac agc caa gag g ag cag gac ttc ctg gcc      192
Gly Arg Leu Ala Ser Ile His Ser Gln Glu G lu Gln Asp Phe Leu Ala
     50                  55              60 agg tat gcc aac aag aag ggc acc tgg att g gc ctc cgg gac ctg gac      240
Arg Tyr Ala Asn Lys Lys Gly Thr Trp Ile G ly Leu Arg Asp Leu Asp
 65                  70              75                  80 aga gag ggg gag ttt atc tgg atg gac gag a ac ccc ctg aac tat agc      288
Arg Glu Gly Glu Phe Ile Trp Met Asp Glu A sn Pro Leu Asn Tyr Ser
                 85                  90              95 aac tgg cgg ccc ggg gag ccc aac aac ggg g gc cag ggc gag gac tgc      336
Asn Trp Arg Pro Gly Glu Pro Asn Asn Gly G ly Gln Gly Glu Asp Cys
         100                 105             110 gtg atg atg cag ggc tcg ggg cag tgg aat g ac gcc ttc tgc ggc agc      384
Val Met Met Gln Gly Ser Gly Gln Trp Asn A sp Ala Phe Cys Gly Ser
     115                 120             125 tcg ctg gac ggc tgg gtg tgt gac cgg ctg g cc acg tgc                  423
Ser Leu Asp Gly Trp Val Cys Asp Arg Leu A la Thr Cys
 130                 135             140

<210> SEQ ID NO 14
<211> LENGTH: 141
<212> TYPE: PRT
<213> ORGANISM: Canis familiaris

<400> SEQUENCE: 14

Leu Trp Met Glu Leu His Val Ser Asn Gly S er Glu Cys Asn Thr Cys
 1               5                  10              15

Pro Glu Lys Trp Leu Asn Phe Gln Arg Lys C ys Tyr Tyr Phe Gly Glu
                 20                  25              30

Glu Pro Lys Lys Trp Ile Gln Ala Arg Phe A la Cys Ser Lys Leu Gln
         35                  40              45

Gly Arg Leu Ala Ser Ile His Ser Gln Glu G lu Gln Asp Phe Leu Ala
     50                  55              60

Arg Tyr Ala Asn Lys Lys Gly Thr Trp Ile G ly Leu Arg Asp Leu Asp
 65                  70              75                  80

Arg Glu Gly Glu Phe Ile Trp Met Asp Glu A sn Pro Leu Asn Tyr Ser
                 85                  90              95

Asn Trp Arg Pro Gly Glu Pro Asn Asn Gly G ly Gln Gly Glu Asp Cys
         100                 105             110

Val Met Met Gln Gly Ser Gly Gln Trp Asn A sp Ala Phe Cys Gly Ser
     115                 120             125

Ser Leu Asp Gly Trp Val Cys Asp Arg Leu A la Thr Cys
 130                 135             140

<210> SEQ ID NO 15
<211> LENGTH: 423
<212> TYPE: DNA
<213> ORGANISM: Canis familiaris

<400> SEQUENCE: 15
gcacgtggcc agccggtcac acacccagcc gtccagcgag ctgccgcaga a ggcgtcatt      60
```

-continued

```
ccactgcccc gagccctgca tcatcacgca gtcctcgccc tggcccccgt t gttgggctc      120 cccgggccgc cagttgctat agttcagggg gttctcgtcc atccagataa a ctcccccctc    180 tctgtccagg tcccggaggc caatccaggt gcccttcttg ttggcatacc t ggccaggaa    240 gtcctgctcc tcttggctgt ggatgctggc cagccgccct tgcagcttgc t gcaggcaaa    300 ccgggcctgg atccacttct tgggctcctc gccgaagtag tagcacttcc t ctggaagtt    360 gagccacttc tcagggcacg tgttacactc ggagccgttg gacacgtgta g ctccatcca    420 cag                                                                    423
```

<210> SEQ ID NO 16
<211> LENGTH: 561
<212> TYPE: DNA
<213> ORGANISM: Canis familiaris
<220> FEATURE:
<221> NAME/KEY: CDS
<222> LOCATION: (1)..(561)

<400> SEQUENCE: 16

```
atg aaa gct cag gac tct gag ctc tcc cag a ac ctg gat gca ctt cgt       48
Met Lys Ala Gln Asp Ser Glu Leu Ser Gln A sn Leu Asp Ala Leu Arg
 1               5                  10                  15 tcg gac ctg aac aac ctc aag tcc cag agc t tg aac gag aga agc aca       96
Ser Asp Leu Asn Asn Leu Lys Ser Gln Ser L eu Asn Glu Arg Ser Thr
             20                  25                  30 gcc ttg cat tca ctg gag aga ctc cag gag g ag gtg gag aag ctg tgg      144
Ala Leu His Ser Leu Glu Arg Leu Gln Glu G lu Val Glu Lys Leu Trp
         35                  40                  45 atg gag cta cac gtg tcc aac ggc tcc gag t gt aac acg tgc cct gag      192
Met Glu Leu His Val Ser Asn Gly Ser Glu C ys Asn Thr Cys Pro Glu
     50                  55                  60 aag tgg ctc aac ttc cag agg aag tgc tac t ac ttc ggc gag gag ccc      240
Lys Trp Leu Asn Phe Gln Arg Lys Cys Tyr T yr Phe Gly Glu Glu Pro
 65                  70                  75                  80 aag aag tgg atc cag gcc cgg ttt gcc tgc a gc aag ctg caa ggg cgg      288
Lys Lys Trp Ile Gln Ala Arg Phe Ala Cys S er Lys Leu Gln Gly Arg
                 85                  90                  95 ctg gcc agc atc cac agc caa gag gag cag g ac ttc ctg gcc agg tat      336
Leu Ala Ser Ile His Ser Gln Glu Glu Gln A sp Phe Leu Ala Arg Tyr
            100                 105                 110 gcc aac aag aag ggc acc tgg att ggc ctc c gg gac ctg gac aga gag      384
Ala Asn Lys Lys Gly Thr Trp Ile Gly Leu A rg Asp Leu Asp Arg Glu
        115                 120                 125 ggg gag ttt atc tgg atg gac gag aac ccc c tg aac tat agc aac tgg      432
Gly Glu Phe Ile Trp Met Asp Glu Asn Pro L eu Asn Tyr Ser Asn Trp
    130                 135                 140 cgg ccc ggg gag ccc aac aac ggg ggc cag g gc gag gac tgc gtg atg      480
Arg Pro Gly Glu Pro Asn Asn Gly Gly Gln G ly Glu Asp Cys Val Met
145                 150                 155                 160 atg cag ggc tcg ggg cag tgg aat gac gcc t tc tgc ggc agc tcg ctg      528
Met Gln Gly Ser Gly Gln Trp Asn Asp Ala P he Cys Gly Ser Ser Leu
                165                 170                 175 gac ggc tgg gtg tgt gac cgg ctg gcc acg t gc                          561
Asp Gly Trp Val Cys Asp Arg Leu Ala Thr C ys
            180                 185
```

<210> SEQ ID NO 17
<211> LENGTH: 187
<212> TYPE: PRT
<213> ORGANISM: Canis familiaris -continued

<400> SEQUENCE: 17

| Met | Lys | Ala | Gln | Asp | Ser | Glu | Leu | Ser | Gln | Asn | Leu | Asp | Ala | Leu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Asp | Leu | Asn | Asn | Leu | Lys | Ser | Gln | Ser | Leu | Asn | Glu | Arg | Ser | Thr |
|     |     |     |     | 20  |     |     |     |     | 25  |     |     |     |     | 30  |     |

| Ala | Leu | His | Ser | Leu | Glu | Arg | Leu | Gln | Glu | Glu | Val | Glu | Lys | Leu | Trp |
|     |     |     | 35  |     |     |     |     | 40  |     |     |     |     | 45  |     |     |

| Met | Glu | Leu | His | Val | Ser | Asn | Gly | Ser | Glu | Cys | Asn | Thr | Cys | Pro | Glu |
|     | 50  |     |     |     |     | 55  |     |     |     |     | 60  |     |     |     |     |

| Lys | Trp | Leu | Asn | Phe | Gln | Arg | Lys | Cys | Tyr | Tyr | Phe | Gly | Glu | Glu | Pro |
| 65  |     |     |     |     | 70  |     |     |     |     | 75  |     |     |     |     | 80  |

| Lys | Lys | Trp | Ile | Gln | Ala | Arg | Phe | Ala | Cys | Ser | Lys | Leu | Gln | Gly | Arg |
|     |     |     |     | 85  |     |     |     |     | 90  |     |     |     |     | 95  |     |

| Leu | Ala | Ser | Ile | His | Ser | Gln | Glu | Glu | Gln | Asp | Phe | Leu | Ala | Arg | Tyr |
|     |     |     |     | 100 |     |     |     |     | 105 |     |     |     |     | 110 |     |

| Ala | Asn | Lys | Lys | Gly | Thr | Trp | Ile | Gly | Leu | Arg | Asp | Leu | Asp | Arg | Glu |
|     |     |     | 115 |     |     |     |     | 120 |     |     |     |     | 125 |     |     |

| Gly | Glu | Phe | Ile | Trp | Met | Asp | Glu | Asn | Pro | Leu | Asn | Tyr | Ser | Asn | Trp |
|     | 130 |     |     |     |     | 135 |     |     |     |     | 140 |     |     |     |     |

| Arg | Pro | Gly | Glu | Pro | Asn | Asn | Gly | Gly | Gln | Gly | Glu | Asp | Cys | Val | Met |
| 145 |     |     |     |     | 150 |     |     |     |     | 155 |     |     |     |     | 160 |

| Met | Gln | Gly | Ser | Gly | Gln | Trp | Asn | Asp | Ala | Phe | Cys | Gly | Ser | Ser | Leu |
|     |     |     |     | 165 |     |     |     |     | 170 |     |     |     |     | 175 |     |

| Asp | Gly | Trp | Val | Cys | Asp | Arg | Leu | Ala | Thr | Cys |
|     |     |     |     | 180 |     |     |     |     | 185 |     |

<210> SEQ ID NO 18
<211> LENGTH: 561
<212> TYPE: DNA
<213> ORGANISM: Canis familiaris

<400> SEQUENCE: 18

| gcacgtggcc agccggtcac acacccagcc gtccagcgag ctgccgcaga a ggcgtcatt | 60 |
| ccactgcccc gagccctgca tcatcacgca gtcctcgccc tggcccccgt t gttgggctc | 120 |
| cccgggccgc cagttgctat agttcagggg gttctcgtcc atccagataa a ctcccccctc | 180 |
| tctgtccagg tcccggaggc caatccaggt gcccttcttg ttggcatacc t ggccaggaa | 240 |
| gtcctgctcc tcttggctgt ggatgctggc cagccgccct gcagcttgc t gcaggcaaa | 300 |
| ccgggcctgg atccacttct tggctcctc gccgaagtag tagcacttcc t ctggaagtt | 360 |
| gagccacttc tcagggcacg tgttacactc ggagccgttg acacgtgta g ctccatcca | 420 |
| cagcttctcc acctcctcct ggagtctctc cagtgaatgc aaggctgtgc t tctctcgtt | 480 |
| caagctctgg gacttgaggt tgttcaggtc gaacgaagt gcatccaggt t ctgggagag | 540 |
| ctcagagtcc tgagctttca t | 561 |

<210> SEQ ID NO 19
<211> LENGTH: 624
<212> TYPE: DNA
<213> ORGANISM: Canis familiaris
<220> FEATURE:
<221> NAME/KEY: CDS
<222> LOCATION: (1)..(624)

<400> SEQUENCE: 19

| cag | aaa | tcc | cag | gct | gcc | cag | gtg | tca | cag | gac | atg | aag | gaa | atc | caa | 48 |
| Gln | Lys | Ser | Gln | Ala | Ala | Gln | Val | Ser | Gln | Asp | Met | Lys | Glu | Ile | Gln |

```
           1               5                    10                   15 gct gaa cag aag aga atg aaa gct cag gac t ct gag ctc tcc cag aac         96
Ala Glu Gln Lys Arg Met Lys Ala Gln Asp S er Glu Leu Ser Gln Asn
                 20                  25                  30 ctg gat gca ctt cgt tcg gac ctg aac aac c tc aag tcc cag agc ttg        144
Leu Asp Ala Leu Arg Ser Asp Leu Asn Asn L eu Lys Ser Gln Ser Leu
         35                  40                  45 aac gag aga agc aca gcc ttg cat tca ctg g ag aga ctc cag gag gag        192
Asn Glu Arg Ser Thr Ala Leu His Ser Leu G lu Arg Leu Gln Glu Glu
     50                  55                  60 gtg gag aag ctg tgg atg gag cta cac gtg t cc aac ggc tcc gag tgt        240
Val Glu Lys Leu Trp Met Glu Leu His Val S er Asn Gly Ser Glu Cys
 65                  70                  75                  80 aac acg tgc cct gag aag tgg ctc aac ttc c ag agg aag tgc tac tac        288
Asn Thr Cys Pro Glu Lys Trp Leu Asn Phe G ln Arg Lys Cys Tyr Tyr
                 85                  90                  95 ttc ggc gag gag ccc aag aag tgg atc cag g cc cgg ttt gcc tgc agc        336
Phe Gly Glu Glu Pro Lys Lys Trp Ile Gln A la Arg Phe Ala Cys Ser
             100                 105                 110 aag ctg caa ggg cgg ctg gcc agc atc cac a gc caa gag gag cag gac        384
Lys Leu Gln Gly Arg Leu Ala Ser Ile His S er Gln Glu Glu Gln Asp
         115                 120                 125 ttc ctg gcc agg tat gcc aac aag aag ggc a cc tgg att ggc ctc cgg        432
Phe Leu Ala Arg Tyr Ala Asn Lys Lys Gly T hr Trp Ile Gly Leu Arg
     130                 135                 140 gac ctg gac aga gag ggg gag ttt atc tgg a tg gac gag aac ccc ctg        480
Asp Leu Asp Arg Glu Gly Glu Phe Ile Trp M et Asp Glu Asn Pro Leu
145                 150                 155                 160 aac tat agc aac tgg cgg ccc ggg gag ccc a ac aac ggg ggc cag ggc        528
Asn Tyr Ser Asn Trp Arg Pro Gly Glu Pro A sn Asn Gly Gly Gln Gly
                 165                 170                 175 gag gac tgc gtg atg atg cag ggc tcg ggg c ag tgg aat gac gcc ttc        576
Glu Asp Cys Val Met Met Gln Gly Ser Gly G ln Trp Asn Asp Ala Phe
             180                 185                 190 tgc ggc agc tcg ctg gac ggc tgg gtg tgt g ac cgg ctg gcc acg tgc        624
Cys Gly Ser Ser Leu Asp Gly Trp Val Cys A sp Arg Leu Ala Thr Cys
         195                 200                 205

<210> SEQ ID NO 20
<211> LENGTH: 208
<212> TYPE: PRT
<213> ORGANISM: Canis familiaris

<400> SEQUENCE: 20

Gln Lys Ser Gln Ala Ala Gln Val Ser Gln A sp Met Lys Glu Ile Gln
 1               5                  10                  15

Ala Glu Gln Lys Arg Met Lys Ala Gln Asp S er Glu Leu Ser Gln Asn
                 20                  25                  30

Leu Asp Ala Leu Arg Ser Asp Leu Asn Asn L eu Lys Ser Gln Ser Leu
         35                  40                  45

Asn Glu Arg Ser Thr Ala Leu His Ser Leu G lu Arg Leu Gln Glu Glu
     50                  55                  60

Val Glu Lys Leu Trp Met Glu Leu His Val S er Asn Gly Ser Glu Cys
 65                  70                  75                  80

Asn Thr Cys Pro Glu Lys Trp Leu Asn Phe G ln Arg Lys Cys Tyr Tyr
                 85                  90                  95

Phe Gly Glu Glu Pro Lys Lys Trp Ile Gln A la Arg Phe Ala Cys Ser
             100                 105                 110
```

```
Lys Leu Gln Gly Arg Leu Ala Ser Ile His Ser Gln Glu Glu Gln Asp
            115                 120                 125

Phe Leu Ala Arg Tyr Ala Asn Lys Lys Gly Thr Trp Ile Gly Leu Arg
        130                 135                 140

Asp Leu Asp Arg Glu Gly Glu Phe Ile Trp Met Asp Glu Asn Pro Leu
145                 150                 155                 160

Asn Tyr Ser Asn Trp Arg Pro Gly Glu Pro Asn Asn Gly Gln Gly
                165                 170                 175

Glu Asp Cys Val Met Met Gln Gly Ser Gly Gln Trp Asn Asp Ala Phe
            180                 185                 190

Cys Gly Ser Ser Leu Asp Gly Trp Val Cys Asp Arg Leu Ala Thr Cys
            195                 200                 205

<210> SEQ ID NO 21
<211> LENGTH: 624
<212> TYPE: DNA
<213> ORGANISM: Canis familiaris

<400> SEQUENCE: 21
gcacgtggcc agccggtcac acacccagcc gtccagcgag ctgccgcaga a ggcgtcatt      60 ccactgcccc gagccctgca tcatcacgca gtcctcgccc tggcccccgt t gttgggctc     120 cccgggccgc cagttgctat agttcagggg gttctcgtcc atccagataa a ctcccccctc    180 tctgtccagg tcccggaggc caatccaggt gcccttcttg ttggcatacc t ggccaggaa     240 gtcctgctcc tcttggctgt ggatgctggc cagccgccct gcagcttgc t gcaggcaaa      300 ccgggcctgg atccacttct gggctcctc gccgaagtag tagcacttcc t ctggaagtt     360 gagccacttc tcagggcacg tgttacactc ggagccgttg acacgtgta g ctccatcca     420 cagcttctcc acctcctcct ggagtctctc cagtgaatgc aaggctgtgc t tctctcgtt    480 caagctctgg gacttgaggt tgttcaggtc cgaacgaagt gcatccaggt t ctgggagag    540 ctcagagtcc tgagctttca ttctcttctg ttcagcttgg atttccttca t gtcctgtga     600 cacctgggca gcctgggatt tctg                                            624

<210> SEQ ID NO 22
<211> LENGTH: 24
<212> TYPE: DNA
<213> ORGANISM: Artificial Sequence
<220> FEATURE:
<223> OTHER INFORMATION: Description of Artificial  Sequence: Synthetic
      Primer

<400> SEQUENCE: 22
gggaaacgga gaagaatcta aaac                                             24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial  Sequence: Synthetic
      Primer

<400> SEQUENCE: 23
gttggagtca cagaggctaa gg                                               22

<210> SEQ ID NO 24
<211> LENGTH: 369
<212> TYPE: DNA
<213> ORGANISM: Canis familiaris
```

-continued

```
<220> FEATURE:
<221> NAME/KEY: CDS
<222> LOCATION: (1)..(369)

<400> SEQUENCE: 24 tcc gag tgt aac acg tgc cct gag aag tgg c tc aac ttc cag agg aag      48
Ser Glu Cys Asn Thr Cys Pro Glu Lys Trp L eu Asn Phe Gln Arg Lys
 1               5                  10                  15 tgc tac tac ttc ggc gag gag ccc aag aag t gg atc cag gcc cgg ttt      96
Cys Tyr Tyr Phe Gly Glu Glu Pro Lys Lys T rp Ile Gln Ala Arg Phe
            20                  25                  30 gcc tgc agc aag ctg caa ggg cgg ctg gcc a gc atc cac agc caa gag     144
Ala Cys Ser Lys Leu Gln Gly Arg Leu Ala S er Ile His Ser Gln Glu
        35                  40                  45 gag cag gac ttc ctg gcc agg tat gcc aac a ag aag ggc acc tgg att     192
Glu Gln Asp Phe Leu Ala Arg Tyr Ala Asn L ys Lys Gly Thr Trp Ile
    50                  55                  60 ggc ctc cgg gac ctg gac aga gag ggg gag t tt atc tgg atg gac gag     240
Gly Leu Arg Asp Leu Asp Arg Glu Gly Glu P he Ile Trp Met Asp Glu
65                  70                  75                  80 aac ccc ctg aac tat agc aac tgg cgg ccc g gg gag ccc aac aac ggg     288
Asn Pro Leu Asn Tyr Ser Asn Trp Arg Pro G ly Glu Pro Asn Asn Gly
                85                  90                  95 ggc cag ggc gag gac tgc gtg atg atg cag g gc tcg ggg cag tgg aat     336
Gly Gln Gly Glu Asp Cys Val Met Met Gln G ly Ser Gly Gln Trp Asn
            100                 105                 110 gac gcc ttc tgc ggc agc tcg ctg gac ggc t gg                         369
Asp Ala Phe Cys Gly Ser Ser Leu Asp Gly T rp
        115                 120

<210> SEQ ID NO 25
<211> LENGTH: 123
<212> TYPE: PRT
<213> ORGANISM: Canis familiaris

<400> SEQUENCE: 25

Ser Glu Cys Asn Thr Cys Pro Glu Lys Trp L eu Asn Phe Gln Arg Lys
 1               5                  10                  15

Cys Tyr Tyr Phe Gly Glu Glu Pro Lys Lys T rp Ile Gln Ala Arg Phe
            20                  25                  30

Ala Cys Ser Lys Leu Gln Gly Arg Leu Ala S er Ile His Ser Gln Glu
        35                  40                  45

Glu Gln Asp Phe Leu Ala Arg Tyr Ala Asn L ys Lys Gly Thr Trp Ile
    50                  55                  60

Gly Leu Arg Asp Leu Asp Arg Glu Gly Glu P he Ile Trp Met Asp Glu
65                  70                  75                  80

Asn Pro Leu Asn Tyr Ser Asn Trp Arg Pro G ly Glu Pro Asn Asn Gly
                85                  90                  95

Gly Gln Gly Glu Asp Cys Val Met Met Gln G ly Ser Gly Gln Trp Asn
            100                 105                 110

Asp Ala Phe Cys Gly Ser Ser Leu Asp Gly T rp
        115                 120

<210> SEQ ID NO 26
<211> LENGTH: 369
<212> TYPE: DNA
<213> ORGANISM: Canis familiaris

<400> SEQUENCE: 26
ccagccgtcc agcgagctgc cgcagaaggc gtcattccac tgccccgagc c ctgcatcat    60
```

```
cacgcagtcc tcgccctggc ccccgttgtt gggctccccg ggccgccagt t gctatagtt       120 caggggttc  tcgtccatcc agataaactc ccctctctg  tccaggtccc g gaggccaat      180 ccaggtgccc ttcttgttgg catacctggc caggaagtcc tgctcctctt g gctgtggat      240 gctggccagc cgcccttgca gcttgctgca ggcaaaccgg gcctggatcc a cttcttggg      300 ctcctcgccg aagtagtagc acttcctctg gaagttgagc cacttctcag g gcacgtgtt      360 acactcgga                                                                369
```